US012737940B2

(12) United States Patent
Jacobs et al.

(10) Patent No.: US 12,737,940 B2
(45) Date of Patent: Sep. 15, 2026

(54) INTERACTIVE FLOW DIAGRAMS FOR HEALTHCARE THROUGH DYNAMIC DATA MODEL GENERATION

(71) Applicant: KONINKLIJKE PHILIPS N.V., Eindhoven (NL)

(72) Inventors: Igor Jacobs, Asten (NL); Gertjan Laurens Schuurkamp, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 18/779,239

(22) Filed: Jul. 22, 2024

(65) Prior Publication Data

US 2025/0029295 A1 Jan. 23, 2025

Related U.S. Application Data

(60) Provisional application No. 63/602,714, filed on Nov. 27, 2023, provisional application No. 63/528,142, filed on Jul. 21, 2023.

(51) Int. Cl.

| | |
|---|---|
| ***G06T 11/26*** | (2026.01) |
| ***G06F 3/0486*** | (2013.01) |
| ***G06F 16/23*** | (2019.01) |
| ***G16H 10/60*** | (2018.01) |

(52) U.S. Cl.

CPC ............ *G06T 11/26* (2026.01); *G06F 3/0486* (2013.01); *G06F 16/23* (2019.01); *G16H 10/60* (2018.01)

(58) Field of Classification Search

CPC ........ G06T 11/26; G06F 3/0486; G06F 16/23; G06F 3/04842; G06F 16/248; G16H 10/60; G16H 40/20; G16H 40/63

See application file for complete search history.

(56) References Cited

U.S. PATENT DOCUMENTS

| | | | | |
|---|---|---|---|---|
| 11,460,973 | B1 * | 10/2022 | Mealin | G06N 3/09 |
| 2017/0039233 | A1 * | 2/2017 | Gauthier | G06F 3/0482 |
| 2018/0113578 | A1 | 4/2018 | Yoon | |
| 2018/0300454 | A1 | 10/2018 | Chan et al. | |
| 2019/0096524 | A1 | 3/2019 | Hu | |
| 2019/0272654 | A1 | 9/2019 | Yaeli et al. | |
| 2020/0050631 | A1 * | 2/2020 | Terblanche | G06Q 10/10 |

(Continued)

OTHER PUBLICATIONS

Neri, Emanuele et al "Radiomics and Liquid Biopsy in Oncology: the Holons of Systems Medicine", Insights Into Imaging, Nov. 2018.

(Continued)

*Primary Examiner* — Phi Hoang

(57) ABSTRACT

In one embodiment, a method for presenting information along plural stages of patient care, the method comprising: initializing an interactive flow diagram (88) based on data, the interactive flow diagram based on an underlying data model, the interactive flow diagram comprising nodes (92) comprising an aggregated visual representation of key-value pairs, columns (90) comprising a stacked bar visualization of the nodes, and links (16) between the nodes; displaying the interactive flow diagram; and dynamically updating the interactive flow diagram based on user interactions with the interactive flow diagram, the interactions resulting in updates to the underlying data model that change an arrangement of at least one of the nodes, the columns, or the links.

20 Claims, 24 Drawing Sheets

(56) References Cited

U.S. PATENT DOCUMENTS

| | | | | |
|---|---|---|---|---|
| 2020/0184691 | A1* | 6/2020 | Bak | G06T 11/26 |
| 2023/0032564 | A1* | 2/2023 | Ishii | G06F 16/9035 |
| 2023/0113933 | A1 | 4/2023 | Beers | |
| 2023/0367784 | A1 | 11/2023 | Jacobs | |

OTHER PUBLICATIONS

Huang, Chih-Wei et al "A Richly Interactive Exploratory Data Analysis and Visualization Tool using Electronics Medical Records", BMC Medical Informatics and Decision Making, 2015, vol. 15, pp. 1-14.

Riehmann, Patrick et al "Interactive Sankey Diagrams", IEEE Symposium on Information Visualization, 2005.

Abukhodair et al., "RadStream: An Interactive Visual Display of Radiology Workflow for Delay Detection in the Clinical Imaging Process", 2017 IEEE Workshop on Visual Analytics in Healthcare, Oct. 1, 2017, pp. 69-76.

Chen et al., "Mapping User Trajectories to Examine Behavior and Outcomes in Digital Health Intervention Data", IEEE VAHC Oct. 20, 2019, pp. 1-8.

* cited by examiner

INTERACTIVE FLOW DIAGRAMS FOR HEALTHCARE THROUGH DYNAMIC DATA MODEL GENERATION

FIELD OF THE INVENTION

The present invention is generally related to healthcare, and more particularly, visualization of healthcare service lines.

BACKGROUND OF THE INVENTION

Clinicians and leadership of patient management systems, including lung nodule management programs, do not have effective ways to collect and report out on clinical, operational and financial key performance indicators. This is due to the lack of structured data, the lack of resources to collect the data, and the lack of accessibility to data. Analytical insights are often not available at all, or require manual capture and aggregation of data from the hospital's information systems. Not only is such effort very labor intensive, data are also often captured in flat data sheets, without the ability to effectively inspect, or report out, on them. As a consequence, it is difficult for clinicians or program management to track how many screening or incidental exams are being reviewed, what are the next steps and follow-up decisions, and what are the outcomes of the tests in the program. This results in a lack of insight in the clinical outcomes of, for instance, the lung nodule management programs, their operational efficacy (including staffing), and revenue.

Philips has a portfolio of enterprise informatics solutions, including clinical informatics solutions, aimed at early cancer detection and orchestration of patient management. An example is the Lung Cancer Orchestrator, which is an integration patient management application for both lung cancer screening and incidental pulmonary findings programs that monitors patients through various steps of their care journey. The application enables tracking of exams, exam results, and decisions made through many steps in the patient journey, including from early identification of an abnormality on an image, to diagnostic follow-up and treatment. The Lung Cancer Orchestrator is built on the Philips IntelliSpace Precision Medicine (ISPM) platform, which is a cloud-based Software as a Service (SaaS) system hosted on the Philips HealthSuite Digital Platform (HSDP). Further information of the Lung Cancer Orchestrator and the ISPM platform may be found on Philips healthcare websites.

Success of early cancer detection programs may depend on the clinical, operational and financial return on investment. However, early detection programs often face challenges with efficiency and cost-effectiveness due, for instance, to the high number of false-positive findings requiring follow-up. Program managers and hospital C-suite need tools to gain insights in program quality, effectiveness, and possible areas of improvement.

SUMMARY OF THE INVENTION

One object of the present invention is to improve upon existing methods for visualizing data for plural stages of subject or patient care. To better address such concerns, in a first aspect of the invention, an interactive flow diagram generation method is disclosed that initializes an interactive flow diagram based on data, the interactive flow diagram based on an underlying data model, the interactive flow diagram comprising nodes comprising an aggregated visual representation of key-value pairs, columns comprising a stacked bar visualization of the nodes, and links between the nodes, displays the interactive flow diagram, and dynamically updates the interactive flow diagram based on user interactions with the interactive flow diagram, the interactions resulting in updates to the underlying data model that change an arrangement of at least one of the nodes, the columns, or the links. With the ability of the interactive flow diagram generation method to dynamically update the underlying data model through user interactions with the diagram, one or more of the limitations of existing Sankey-based diagrams including limited interactivity, scalability, and flexibility are overcome.

In one embodiment, the interactive flow diagram generation method provides aggregated information based on user input over one of the nodes, the aggregated information providing further detail about the one of the nodes. By enabling the visualization of aggregate information in the interactive flow diagram, additional diagnostics for a patient may be readily accessed.

In one embodiment, the interactive flow diagram generation method further comprises isolating a sub-population of one of the nodes based on user input at the one of the nodes. For instance, using a simple user input, such as a mouse click, enables the isolation of sub-populations to enable one to hone in on a particular disorder, or more generally, characteristic, common among the groups.

In one embodiment, the interactive flow diagram generation method further comprises repositioning or removing one of the columns based on user input corresponding to drag-and-drop functionality. The removal or repositioning of columns enables the user to flexibly tailor the presentation of information in a manner suitable to the user using the convenient and familiar user interactive technique of drag and drop functionality.

In one embodiment, the interactive flow diagram generation method displays the interactive flow diagram as a standalone analytics tool, or one or a combination of, in conjunction with an existing analytics application as a custom chart or in conjunction with a patient management application. This adaptability to a variety of application platforms permits ready acceptance in the medical or clinical field.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

FIG. 14 is a screen diagram that illustrates an embodiment of the example interactive flow diagram enabling retrieval of individual patient identifiers among selected cohorts, in accordance with an embodiment of the invention.

DETAILED DESCRIPTION OF EMBODIMENTS

Figure 1:
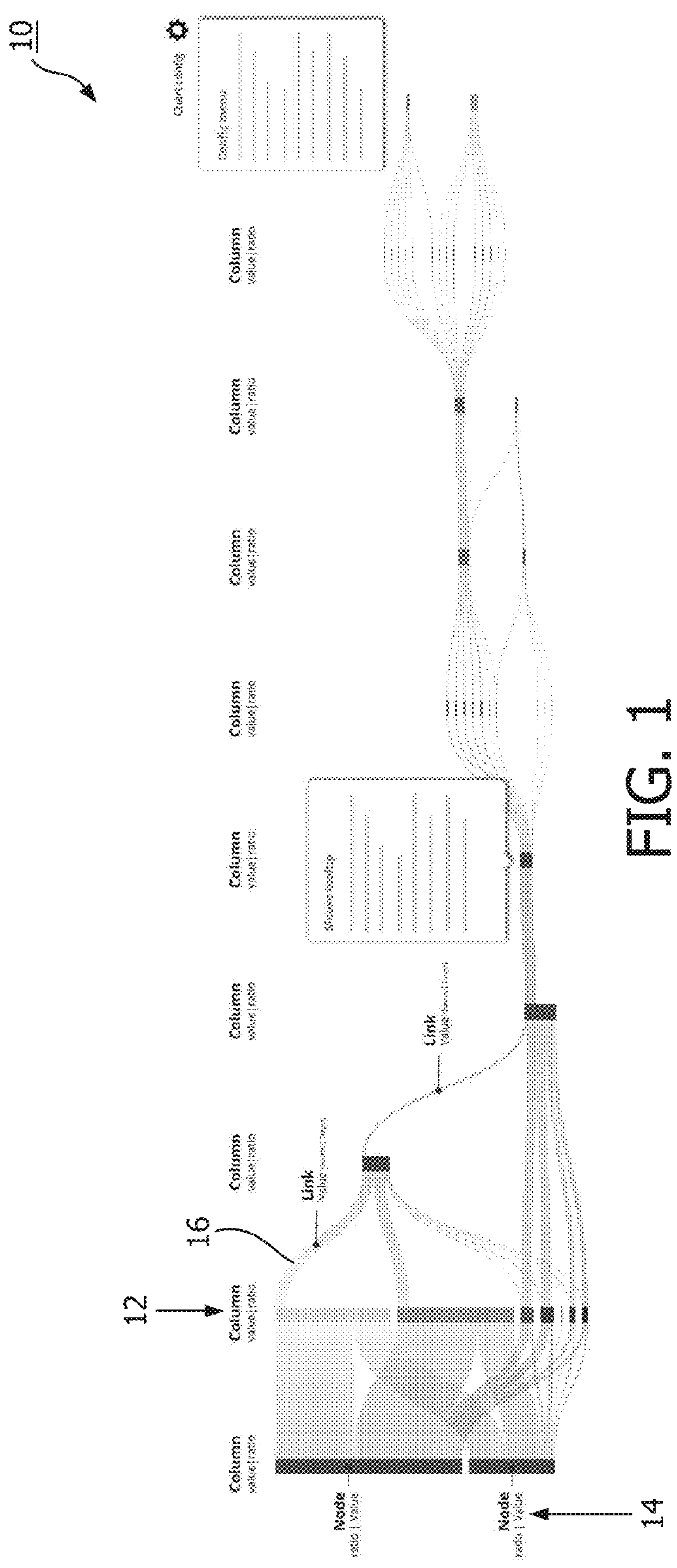
FIG. 1 is a schematic diagram that illustrates an example patient flow diagram based on a Sankey diagram format, in accordance with an embodiment of the invention.

Disclosed herein are certain embodiments of an interactive flow diagram generation system and method that may be implemented in a cloud-based patient health platform. The analytics application is described here in the context of Philips IntelliSpace Precision Medicine (ISPM), which is a cloud-based Software as a Service (SaaS) system hosted on the Philips HealthSuite Digital Platform (HSDP), though it should be appreciated that functionality of the interactive flow diagram generation system may be implemented in other platforms in some embodiments, such as the Philips HealthSuite Diagnostics (HSD) platform. In the example embodiments described herein, the interactive flow diagram generation system is described in conjunction with (embedded in, or as a stand-alone component coupled thereto) the Philips Lung Cancer Orchestrator (LCO), which is an integrated lung cancer patient management system for lung screening and incidental pulmonary findings programs that monitors patients through various steps of their lung cancer detection, diagnosis and treatment decision journey. Note that the examples described below are for illustration, and it should be appreciated that some embodiments of the interactive flow diagram generation system may be used in conjunction with other and/or additional lung cancer management systems, other and/or additional applications across the lung care continuum, and/or in cooperation with patient management systems dedicated to or involved in patient care for other diseases or health issues.

The interactive flow diagram generation system provides an interactive framework for visualization of healthcare service lines, from the moment of inclusion in the program until a definitive diagnosis is reached. The interactive flow diagram generation system builds upon a Sankey diagram visualization, but is unique in its configurability and interactivity due to the underlying framework that enables real-time modelling of the data. Explaining further, existing Sankey diagrams are described by an underlying data model that is predefined. In contrast, certain embodiments of an interactive flow diagram generation system use a dynamically-updated data model, which beginning with a user-defined configuration, the system is configured to read data (e.g., from a flat table) and search for available data categories. Subsequently, based on user interaction with the interactive flow diagram (e.g., switching the relational order of displayed data categories, inclusion and/or exclusion of data categories, etc.), the underlying data model is updated. The interactive flow diagram generation system is scalable to other disease areas and applicable to other domains than healthcare.

Digressing briefly, an important component for driving lung nodule management programs is having operational and clinical insights in the efficacy and quality of lung nodule management. These insights may be used to monitor lung nodule management programs, report to internal and external stakeholders, and drive quality improvement initiatives. As explained above, clinicians and leadership of patient management systems, including lung nodule management programs, do not have effective ways to collect and report out on clinical, operational and financial key performance indicators. Analytics applications, in general, resolve the problem of a lack of clinical, operational and financial insight in the performance of complete health care services lines (e.g., care that is centered on the patient's unique condition or disease and is integrated and coordinated across a healthcare system). On top of that, certain embodiments of the interactive flow diagram generation system provides an interactive flow diagram that provides a full overview of the flow of patients in the early detection programs (or other care service lines), from entry to outcomes, without requiring multiple pages and graphs. Also, the interactive flow diagram enables drilling down into the flow and outcomes of sub-populations and comparing them amongst each other. Indeed, not only may the interactive flow diagrams provide a helpful visualization tool for an analytics application, the interactive flow diagrams may serve the function of an analytics application, providing a more advanced visualization than, say, classic BI dashboards.

As indicated above, certain embodiments of the interactive flow diagram generation system renders interactive flow diagrams that overcome limitations of existing Sankey diagrams. For instance, Sankey diagrams are designed to visualize the flow of a set of values or resources from a common starting point to an endpoint. Sankey diagrams display several entities (nodes), linked through flows, both being proportional to their volume. However, there exists limitations of existing Sankey diagrams that the interactive flow diagrams of the present disclosure overcome, including limited interactivity, limited scalability, and limited flexibility. As to limited interactivity, even though Sankey diagrams may offer some interactivity, the underlying data is premodelled. Also, the displayed data categories in existing Sankey diagrams typically have a fixed order with limited freedom to rearrange columns or to add/remove endpoints. As to limited scalability, Sankey diagrams of complex data quickly become cluttered and hard to read due to the large number of nodes and flows. As to limited flexibility, Sankey diagrams provide limited flexibility of examining the data from multiple angles or perspectives, or possess limitations in analyzing the data at the level of various population cohorts and focusing on only a sub-set of the data categories present in the entire dataset. In contrast, certain embodiments of the interactive flow diagram generation system enable interactivity through real-time construction of a flow diagram visualization model (i.e., the underlying data model that describes the interactive flow diagram and the relations between displayed categories). For instance, as briefly explained above, the starting point may be a flat table (e.g., a data structure consisting of rows and columns with 'flat' values, without nested data structures or formulas), from which an algorithm builds up the model by searching for relations after being initialized via a configuration file. The user is then provided the ability to interactively select which endpoints shall be excluded from the diagram, or be excluded from flowing downstream, enabling a more effective representation of the funnel from entry to outcomes.

Having summarized certain features of an interactive flow diagram generation system of the present disclosure, reference will now be made in detail to the description of an interactive flow diagram generation system as illustrated in the drawings. While an interactive flow diagram generation system will be described in connection with these drawings, there is no intent to limit it to the embodiment or embodiments disclosed herein. For instance, the interactive flow diagram generation system may be applicable to various medical domains, including oncology, cardiovascular, etc. That is, though described in the context of lung analytics, the interactive flow diagram generation system may be used with other analytics applications (e.g., genome analytics, prostate analytics), used as an analytics application, or may be for use with other disease orchestrators (e.g., in addition to or as an alternative to a lung cancer orchestrator, prostate cancer orchestrator, oncology orchestrator, cardiology care orchestrator, neurology orchestrator, etc.). Further, although the description identifies or describes specifics of one or more embodiments, such specifics are not necessarily part of every embodiment, nor are all of any various stated advantages necessarily associated with a single embodiment. The intent is to cover alternatives, modifications and equivalents included within the principles and scope of the disclosure as defined by the appended claims. As another example, two or more embodiments may be interchanged or combined in any combination. Further, it should be appreciated in the context of the present disclosure that the claims are not necessarily limited to the particular embodiments set out in the description.

FIG. 1 is a schematic diagram that illustrates an example patient flow diagram 10, which is also reflective of the structure of a Sankey diagram, which forms the basis for the interactive patient flow diagram described herein. The patient flow diagram 10 comprises columns 12, nodes 14, and links 16. The patient flow diagram 10 comprises a flow chart that represents clusters (columns 12) of nodes 14, and the links 16 between the nodes 14 represent changes in the composition of these columns 12. The height of a column/node represents its size, and the height of a link 16 represents the size of the components contained in both nodes 14 connected by the stream field.

Each column 12 comprises a stacked bar data visualization of nodes 14. The horizontal positional order of the columns 12 is described in a config relationPath (e.g., Column 1=Gender, Column 2=Race, Column 3= . . . ), which comprises an ordered list defining or describing the order of the columns in a configuration (config) file (described further in association with FIGS. 2A-2B).

Each node 14 comprises an aggregated visual representation of key-value pairs. The height of a node 14 is calculated based on aggregated value ratios. The vertical order can be defined in the config as illustrated by the following example:

```
Column = Gender | value: 200
  Node 1 = Male | value 50 | ratio 25%
  Node 2 = Female| value 150 | ratio 75%
```

The height/thickness of a link 16 represents the value (difference between source and target node) of the components contained in both blocks connected by the link 16 as illustrated by the following example:

```
Node Gender <-> Node Race
  Node gender_male <-> node race Caucasian
  Node gender_male <-> node race Asian
  Node gender_female <-> node race_Caucasian
  Node gender_female <-> node race_Asian
```

Figure 2A:
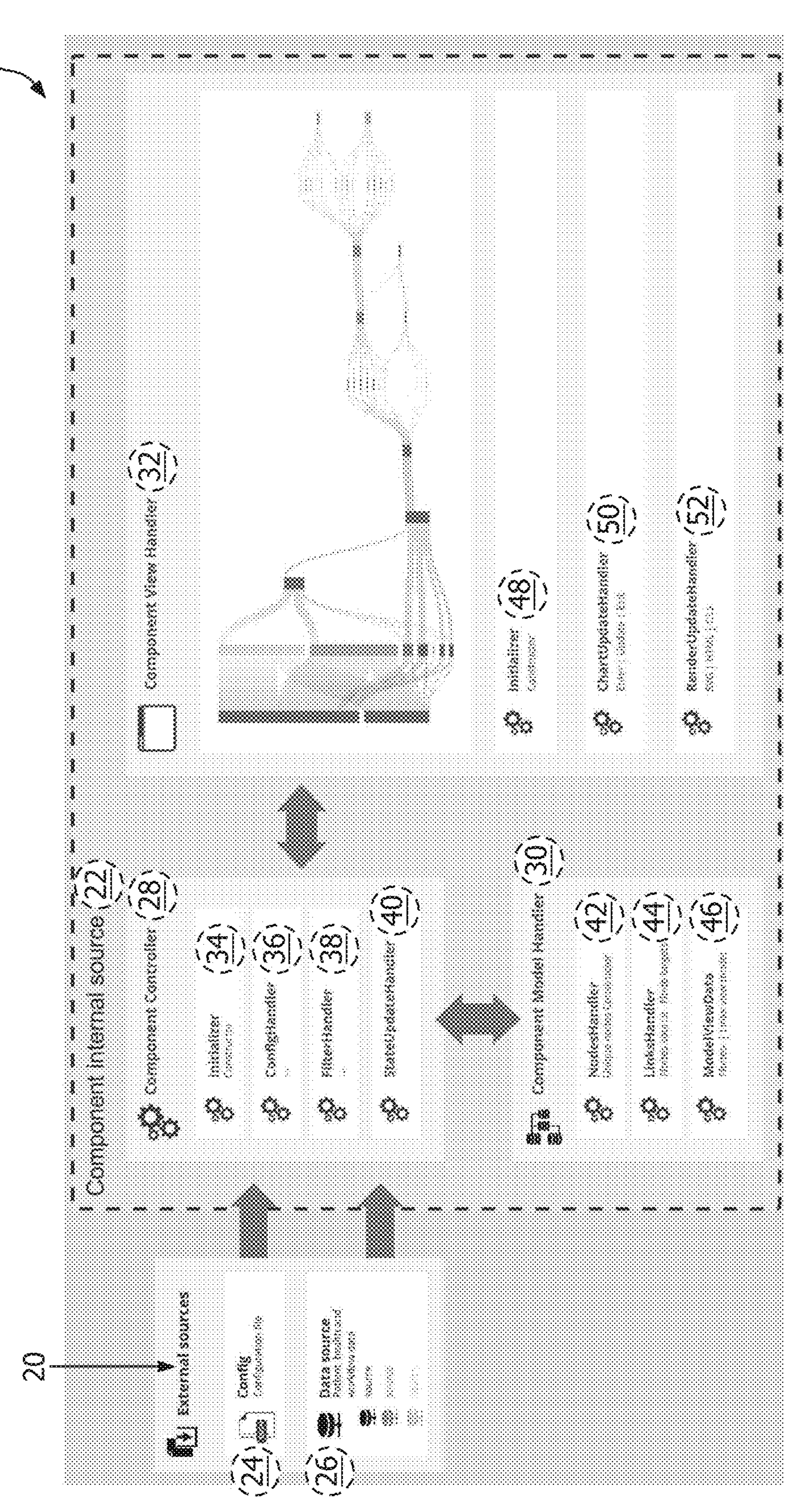
FIG. 2A is a schematic diagram that illustrates an embodiment of an example interactive flow diagram generation system, in accordance with an embodiment of the invention.

FIG. 2A is a schematic diagram that illustrates an embodiment of an example interactive flow diagram generation system 18. In one embodiment, the interactive flow diagram generation system 18 generates a visualization model (underling data model) and enables user interactions with an interactive flow diagram (e.g., subject or patient flow chart). The interactive flow diagram generation system 18 comprises external sources 20 that serve as a source of information to a component internal source 22. The external sources 20 comprise a configuration file 24 and data source 26. The configuration file 24 contains a codified description of the patient flow chart, comprising a list of excluded values, a list of available columns, a relation path (i.e., the order of the columns), order information (i.e., the order of data elements within the columns), and aggregation information. The list of excluded values comprises a non-ordered list of values that are not to be included in the flow diagram. The list of available columns comprises a non-ordered list of columns (i.e., data categories) that are available and can be added in the flow diagram. The relation path comprises an ordered list of columns that describes their default order of display in the flow diagram. The order information describes the order in which the nodes are displayed vertically. The aggregation information describes additional information (e.g., data categories and values) that can be displayed in a tooltip. The aggregation information is for cases where, for a specific data category, additional data exists. For example, the aggregation information specifies, for the data category, diagnostic follow-up (e.g., more detailed data is available specifying all or more diagnostic follow-up exams). One mechanism for accessing such information, as explained further below, is via user input such as maneuvering a mouse over (hovering over) a category using a tooltip/dialogue window, the tooltip/dialogue functionality enabled via, for instance, HTML/Javascript.

As a simple illustration of example functionality/arrangement of the configuration file 24 assume the following data structure (TABLE 1 below);

TABLE 1

| | Column 1 - Fruits | Column 2 - Beers | Column 3 | Column 4 | Column x |
|---|---|---|---|---|---|
| Row 1 | Apple | Ale | R1C3 | R1C4 | Value x |
| Row 2 | Pear | Lager | R2C3 | R2C4 | R2Cx |
| Row 3 | Banana | IPA | R3C3 | NA | R3Cx |
| Row x | Fruit x | Beer x | RxC3 | None | RxCx |

As shown in TABLE 1, some example values (e.g., apple, ale, etc.) are shown for some column/row (C/R) entries, with generic representations (e.g., R1C3, R2C4) also denoted for brevity. An example configuration file 24 may be represented in pseudo code as follows (with comments added after "//" for further explanation):

```
reportConfig.JSON (external fetched file)
  "excludeKeys": [NA, "", void, Blank, None], // values that are not
accepted in the sequential flow
  "relationPath": [
    {endPoint: Fruits (column 1), orderBy: {sourceKey,
ascending}, fiterProps:null},
    {endPoint: Column 3, orderBy: {sourceKey, descending},
  fiterProps:null},
    {endPoint: Column 2, aggregateBy: {endpoint: column x,
fiterProps:null},
    {endPoint: Column 4, filterProps:null},
    {endPoint: Column x, filterProps:null},
      ],
  "availableEndpoints: [ ]
  //relationPath: Ordered list of relational columns
  //availableEndpoints: An unordered list of table columns that may
be activated in the patient flow
  //endpoint: Specific table column
  //orderBy: Sorting based on the values or keys
  //aggregateBy: Data aggregation for a specific column that may be
displayed in the tooltip (as text or a chart)
```

Figure 2B:
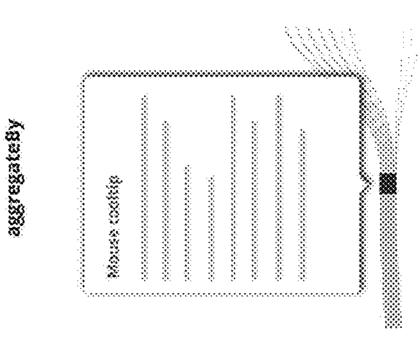
FIG. 2B is a visual illustration corresponding to the description for FIG. 2A that reflects the ordering of columns and the orderBy and aggregateBy functions, in accordance with an embodiment of the invention.
Figure 2B:
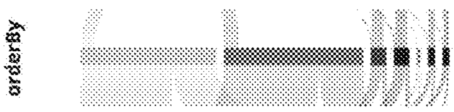
Figure 2B:
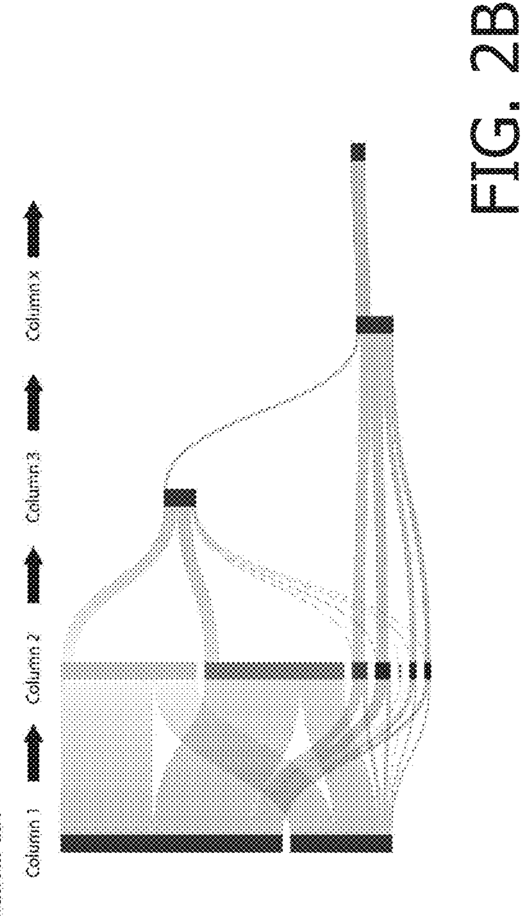

FIG. 2B graphically illustrates the relationPath, orderBy, and aggregateBy functionality described above.

In the case of lung screening, an example configuration file 24 may take the following illustrative (non-limiting) form:

```
"group":{"key":"LUNG_Screening", "label":"Lung Screening"},
  "excludeFilters":null,
  "excludeKeys":["NA", ""],
  "relationPath":[
    {"endpoint":"screening_cycle",
         "orderBy":["sourceKey", "asc"]
    },
    {"endpoint":"screening_lung_rads_score_display",
        "aggregateBy":{"endpoint":"practitioner_name",
"header":"Practitioner", "type":"Events"},
        "orderBy":["sourceKey", "asc"]
    },
    {"endpoint":"screening_ct_other_findings_detected",
         "aggregateBy":{"endpoint":"screening_ct_other_finding
s_display", "header":"CT findings", "type":"Events"}
    },
    {"endpoint":"revered_to_additional_diagnostics",
         "aggregateBy":{"endpoint":"additional_diagnostics_typ
es", "header":"Diagnostic Events", "type":"Events"}
    },
    {"endpoint":"revered_to_tissue_diagnostics",
         "aggregateBy":{"endpoint":"pathology_technique",
"header":"Pathology events", "type":"Techniques"}
    },
    {"endpoint":"pathology_event_tissuediagnosis_display",
         "aggregateBy":{"endpoint":"pathology_technique",
"header":"Pathology events", "type":"Techniques"}
    },
    {"endpoint":"is_diagnosed_with_cancer",
         "aggregateBy":{"endpoint":"pathology_event_tissuedia
gnosis_display", "header":"Pathology findings", "type":"Findings"}
    },
    {"endpoint":"is_diagnosed_with_lung_cancer"},
    {"endpoint":"stage_group_display",
"orderBy":["sourceKey", "desc"]},
    {"endpoint":"stage_phase_detection"},
    {"endpoint":"time_to_diagnosis",
         "aggregateBy":{"endpoint":"additional_diagnostics_typ
es", "header":"CT findings", "type":"Events"}
    }
    ],
  "availableEndpoints":[
    {"endpoint":"race", "orderBy":["sourceKey", "desc"]},
    {"endpoint":"gender", "orderBy":["sourceKey", "desc"]},
    {"endpoint":"copd", "orderBy":["sourceKey", "desc"]},
    {"endpoint":"logical_year", "orderBy":["sourceKey",
"desc"]},
    {"endpoint":"facility_name"},
    {"endpoint":"organization_name"},
    {"endpoint":"screening_event_category_display"},
    {"endpoint":"number_of_screening_cycles",
"orderBy":["sourceKey", "desc"]},
    {"endpoint":"practitioner_name"},
    {"endpoint":"observation_smoking_cessation"},
    {"endpoint":"screening_exam_result"}
    ]
```

Note that the example configuration file 24 for lung screening as shown above is merely an illustrative example, and in some embodiments, configuration files may differ based on the desired diagnostics.

The data source 26 contains the data that is ingested into the flow diagram. The data source 26 may be a flat file database (e.g., an excel spreadsheet) or a relational (SQL) database. The data source 26 may be manually filled by the user or populated through automated extraction of data from a hospital information system or patient management software applications.

The component internal source 22 comprises a component controller 28, component model handler 30, and component view handler 32. The component controller 28 comprises listeners that interface between the model handler 30 and component view handler 32. The component controller 28 comprises an Initializer 34, and three (3) main controllers, namely, the ConfigHandler 36, FilterHandler 38, and a StateUpdateHandler 40.

The Initializer 34 loads the default configuration and initiates the default view of the flow diagram.

The ConfigHandler 36 generally is responsible for enabling the repositioning of columns and adding/removing columns. That is, the ConfigHandler 36 responds to user interaction with the flow diagram, enables addition of columns by selection of data categories from a user interface list, enables removal of columns by dragging columns into a trash bin, and enables repositioning of the columns, by altering the order of the columns (e.g. through drag-drop interaction). The ConfigHandler 36 (also, controller.configHandler) listens to (monitors) user interactions (e.g., drag and drop interactions) with the flow diagram. In one embodiment, the ConfigHandler 36 listens to callback properties on the relationPath and availableColumns and reconstructs the configuration. Example pseudo code for achieving ConfigHandler functionality is illustrated below:

```
controller.configHandler(newRelationPath, newColumns) {
//if newColumns = = false there is only reposition and/or removal of
columns by drag and drop user interactions
If(!newColumns) {
//compare and synchronize the config.relationPath list order equal to
newRelationPath
//if there is an endpoint mismatch between the two lists, the endpoint is
added to the config.availableEndpoints and removed from the
config.relationPath
each(newRelationPath => (endpoint, newIndex) ) {
  variable match = findInList(config.relationPath, (endpoint ===
  endpoint);
if(match)
  match.index=newIndex; //set the new order index of the column
else(!match)
  config.availableEndpoints.add(endpoint);
}
//re-order the config.relationPath to the new synced indexes
order(config.relationPath, byIndex)
variable modelViewData=modelHandler.getModelViewdata(config,
data); //data is the source table
//update the view by through the stateUpdateHandler
stateUpdateHandler.update(config, modelViewData)
}
}
```

The FilterHandler 38 (also, controller.filterHandler) enables addition and removal of filters by clicking on a node, multiple nodes or link(s). Filtering enables selection of a sub-set of the data and visualization of only the selected subset of data in the flow diagram, and display of the characteristics of the selected sub-set of data in other charts that are driven by interaction with the flow diagram. In one embodiment, the FilterHandler 38 listens to the user interactions, Node mouse Click, and receives properties of the endpoint and node that is clicked, and checks if the filter for that node needs to be activated or de-activated before it calls the modelViewData. Example pseudo code for the controller.filterHandler is illustrated below:

```
//Callback properties (endpoint, node) of the mouse click (see
ViewHandler | User interactions | Nodes Filtering)
controller.filterHandler(endpoint, node) {
//check in the config.relationPath.filterOptions if the node key is active
//If the node key is found in the filterOptionsList, de-activate the filter by
removing it from the list
//If the node key is not found in the filterOptionsList, activate the filter by
adding it to the list
variable clickedColumn = findInList(config.relationPath, item =>
item.endPoint === endpoint)) //find the clicked column/endpoint in the
relation path
variable active = findInList(clickedColumn.filterOptions, item =>
(item.key === node.key))
if(active === true) remove(clickedColumn.filterOptions[node.key])
//De-activate the node filter by removing the node.key from the filter
options
if(active === false) add(clickedColumn.filterOptions[node.key])
//Activate the node filter by adding the node.key to the filter options
//the filterOptions in the config.relationPath are updated and passed to the
modelViewData
variable modelViewData=modelHandler.getModelViewData(config, data);
//data is the source table
//update the view by through the stateUpdateHandler
stateUpdateHandler.update(config, modelViewData)
}
```

The StateUpdateHandler 40 dynamically updates the data model describing the structure of the flow diagram, which is subsequently parsed to the modelView. The StateUpdateHandler 40 (also, controller.StateUpdateHandler) listens to the configHandler and FilterHandler and updates the view with the new properties. The StateUpdateHandler 40 is also responsible for initiation of the component. Example pseudo code for the controller.StateUpdateHandler is illustrated below:

```
//Initiation
stateUpdateHandler.init(config, data) {
viewHandler.create(htmlElement) // constructs the view state
variable modelViewData=modelHandler.getModelViewData(config,
data); //data and configuration are outside fetched files
}
//Updates the view when config or filter states change
stateUpdateHandler.update(config, modelViewData) {
viewHandler.update(htmlElement, modelViewData);
}
```

The component model handler 30 comprises a NodesHandler 42, LinksHandler 44, and ModelViewData 46. In general, the NodesHandler 42 is a function that iteratively processes each row from the table and creates the unique nodes based on the relationPath. The NodesHandler 42 generates a unique list of nodes, through an iteration based on the relation path in the configuration file. Subsequently, the NodesHandler 42 processes the data source to search for data categories described in the source file. If an encountered data category does not exist yet, the NodesHandler 42 creates a new node with a unique identifier and a statistic describing the count. Throughout the processing, every time a node already exists, the NodesHandler 42 updates the characteristic and statistic. As an example illustration:

```
relationPath=Gender | metric=Male;
if    node[gender_male] does not exist
      new node={ id:gender_male, value:1, columnOrder:1, nodeOrder:3,
characteristics:{any} }
else
      add 1 to node[gender_male] value
```

In one embodiment, the functionality of the NodesHandler 42 (also, nodesHandler) involves several steps, as illustrated by the example process and pseudo code illustrated below:

```
step 1: Declare the collector map for the nodes and links.
variable nodesIdMap //collection of unique nodes
variable linksIdMap //collection of unique links
step 2: Iterate each row in the table and pass the row to the nodeCreate
function
For each (row in table) -> { nodesHandler(row) }
step 3: Iterate the relationPath to create or modify unique nodes. Each node
is uniquely identified by a combination of the key and value of the cell (e.g.,
nodeId=Fruits__Apple)
Function nodesHandler(row){
// iterate over each endpoint in the config.relationPath. The active index is the
sourceNode and the next index is the targetNode
For each(endpoint in relationPath) ->{
// check if key is not listed in config.excludeKeys
if( row[endpoint] ) equals config.excludeKeys['any'] -> break //exit and check
the next index endpoint in the relationPath of the active row
// check if the source node exists in the nodesIdMap
var sourceNodeID=endpoint+__+row[endpoint] //(e.g.,
sourceNodeID=Fruits__Banana)
//in case nodesIdMap(sourceNodeID) does not exist, create a new entry
if( !nodesIdMap[sourceNodeID] ) -> nodesIdMap[sourceNodeID] =
createNode( sourceNodeID, endpoint, row(endpoint) ) //create a new node in
nodesIdMap
//check if filterOptionsKey is not active and add +1 value to the sourceNode
count. Filterkey options in the config.relationPath are set by the
controller.filterHandler (see controller)
if( row[endpoint] !== row[endpoint].filterOptions[any] )
nodesIdMap[nodeID].value ++;
// check if the target node exists in the nodesIdMap, if not iterate the
config.relationPath to see if other followup connections are possible
let currentIndex= relationPath[currentIndex]
while (currentIndex < relationPath[lastIndex] ) {
var targetEndPoint= relationPath[currentIndex+1].endpoint
var targetKey= row(relationPath[currentIndex+1].endpoint
var targetNodeID=targetEndPoint+__+targetKey
// check if key is not listed in config.excludeKeys
if( targetKey ) equals config.excludeKeys['any'] -> currentIndex++ //exit and
check the next source endpoint in the relationPath
//in case nodesIdMap(targetNodeID) does not exist
if( !nodesIdMap[targetNodeID] ) -> nodesIdMap[targetNodeID] = createNode(
targetNodeID, targetEndpoint, targetKey ) //create a new node in nodesIdMap
}
//if both source node and target node exist build the linked model
if(nodesIdMap[sourceNodeID] && nodesIdMap[targetNodeID] ) -> linksHandler(
nodesIdMap[sourceNodeID], nodesIdMap[targetNodeID] );
}
```

The following pseudocode applies to the nodesHandler:

```
Function createNode(nodeID, endpoint, key){ nodesIdMap[nodeID]={
id: nodeID,
endpoint: endpoint, //column key/label
key: key, //cell key/value
value: 0 //aggregation count
aggregationBy:null //if set in the config.relationPath this object will be
used for storing the data
}
}
```

The LinksHandler 44 generates a unique list of links, through an iteration based on the relation path, and aggregates the total count volume of the link. A search algorithm detects the shortest possible connection between nodes. If no connection can be found (or is excluded through the configuration file), the link is not created. Every time a link is found, the value of the link (e.g., count) is updated. The structure is based on source-target logic. As an example illustration:

```
relationPath=Gender (Male) <-> Race (Asian);
if        link[gender__male - race__asian ] does not exist
```

-continued

```
          new link=
          { sourceNode: node[gender__male]
          targetNode: node[race__asian]
          value: 1
          }
else
          add 1 to link[gender__male - race__asian ] value
```

Continuing the example steps in the process with illustrative pseudo code for LinksHandler functionality:

```
step 4: LinksHandler
LinksHandler(sourceNode, targetNode) -> {
// source and target nodes are stored in the nodesIdMap
var linkID=sourceNode.id+|+targetNode.id; //eg
Fruits__banana|Beers__Ipa
//check if the link exists in the linksIdMap, if not create a new link
entry
if( !linksIdMap[linkID] ) -> linksIdMap[linkID] = (linkID,
sourceNode, targetNode) //create a new node in nodesIdMap
function createLink(id, sourceNode, targetNode){
```

-continued

```
  linksIdMap[linkID] ={
    id: linkID,
    source: sourceNode,
    target:targetNode, value: 0
    }
    }
  //check if values for the sourceNode not equal to -0 and Add +1 value
to the link every time the function is called. If the value of the node = 0,
that means a node filter is active
  If(source.Node.value > 0) linsIdMap[linkID].value++;
  }
  step 5: ModelViewData 46. After sorting the collections based on the
config.relationPath.order the NodesIdMap and the LinksIdMap into one
object that can be passed and processed by the view handler.
  variable modelViewData={config, nodesIdMap, linksIdMap}; // this
object is passed to the controller.stateUpdateHandler that interfaces with
the view
```

The Component Model Handler 30 returns the ModelViewData 46, comprising the nodes map and links map. In some embodiments, the Component Model Handler 30 provides the user the ability to exclude relations between values such that they are not displayed in the interactive flow diagram. For instance, in one embodiment, the configuration file describes a generic exclusion (e.g., categories that are always excluded from a process of generating the patient flow, such as NA values, data voids, etc.). The Component Model Handler 30 obtains this information from the configuration file, where the user may specify this information.

The Component View Handler 32 comprises an Initializer 48, ChartUpdateHandler 50, and RenderUpdateHandler 52. The Initializer 48 sets HTML and Cascading Style Sheets (CSS) properties (dims, style, . . . ), sets SVG structure and properties, sets chart properties, and sets additional properties (tooltip, drawUtils, colorPallets, Transitions).

The ChartUpdateHandler 50 comprises a Responsiveness updater that updates SVG structure and properties (dims, scale, domains, . . . ), updates the model view flow chart, including columns, nodes, links (position, size, color, . . . ), descriptives (headers, labels, tooltip content, . . . ), and Config logic (applied filters).

The RenderUpdateHandler 52 sets and updates SVG column groups (e.g., data binding, header and filter, drag-and-drop, call-back), sets and updates SVG nodes (e.g., data binding, nodes and labels, mouse actions (enter, move, over, out, right-click, . . . ), filter, call-back), and sets and updates SVG links (e.g., data binding and mouse actions (enter, move, over, out, right-click, . . . ).

Example algorithms/pseudo code for the various functionality of the Component View Handler 32 are described below. Initially, to get all of the visual properties of the patient flow, the nodesIdMap and linksIDMap are passed to an existing module, referred to as a d3-sankey module, information of which may be obtained from published documentation (e.g., the Internet (e.g., github)). The d3-sankey module calculates the visual position properties of each node and link. A description of the process utilizing the d3-sankey module is described below, with accompanying example pseudo code for the Component View Handler 32. Step 1 gets and sets Sankey properties:

```
sankeyProperties = SankeyChart({ nodes:
nodesIdMap,
links: linksIdMap
}, { })
```

The SankeyChart function returns an array of nodes and links. Each node gets position properties: x0, y0, x1, y1. Each link gets position properties: y0, y1. The x-positions are stored in the nodes that are stored in the link object (e.g., from linksHandler) and referenced to the nodesIdMap.

Step 2 gets and sets custom visual properties for the nodes and column groups. After retrieving the position properties from the d3-sankey module, a second processing is performed. Based on each endpoint (column), the nodes are collected into groups:

```
  Add sankeyProperties.gColumns //g stands for svg group that is
  representing an svg domain element
  //collect and group nodes together
  For each(node in sankeyProperties.nodes ->{
    node.properties={ width:(node.x1-node.x0),
    height:(node.y1-node.y0),
  color:(reference to color pallet , ......)} //add custom visual properties to
  the node
  //check if group exist by the endpoint, the endpoint is the column name
defined in the relation table
if( !gColumns[node.endpoint] ) gColumns[node.endpoint]={
endpoint:node.endpoint,
  properties:{ x:node.x, y:node.y, label, descriptives, ...} //add custom
(visual) properties,
  header: node.header //descriptives are stored in a separate textIdMap
and/or stored in the source table,
  nodes:[ ] //array collection of the nodes that are visualized as svg dom
elements
  value:0
}
  gColumns[node.endpoint] .add(node) //add the node to the nodes list
  gColums[node.endpoint] .value += node.value //calculate the total
value of the column
```

Step 3 in the d3-Sankey processing gets and sets custom visual properties for the links. In the links collection, the source and target nodes are stored as references to the nodes map. Visual node properties are thus accessible and may be used to set the visual properties of the links. Example pseudo code is as follows:

```
For each(link in sankeyProperties.links ->{
link.color=link.sourceNode.properties.color
if( link.sourceNode.properties.color !==
link.targetNode.properties.color)
link.color=calculateGradient(source, target)
link.label= //set the displayed label
....
}
```

As to the chart rendering functionality of the Component View Handler 32, example steps in the process and illustrative pseudo code are described below. In Step 1, an svg container is created:

```
  //Create and append svg dom elements to the HTML div element
  variable svg=div.append('svg') //div is passed through by a framework
(or can be selected by javascript (not part of the component))
  variable gLinks=svg.append('g') //svg g element for the connecting link
lines
  variable gColumns=svg.append('g') //the nodes will be nested in each
column
```

In Step 2, the gColumns are appended with the d3 selections and the column data is bound to the objects:

```
variable gColumns
=svg.selectAll(gColumn).data(sankeyProperties.gColumns) //based on the
amount of data entries svg g elements are created
  // append the svg elements and set the attributes stored in each data
element d
  gColumns.enter( ).append(g)
  .attr(id, gColumn)
  .attr(x, d => d.x).attr(y, d => d.y)
  .each(d, index =>{
  //iterate each g data element and add specific items like header, icons
lables etc.
  //examples
  var g=d3.select(this); //selection of svg g element
  g.append(text).attr(x, d.x).attr(y, d.y-64).text(d.header)
  g.append(icon)   //icon to reset filter column options
  g.append(item) ....
  //in the data entry d are the separate nodes stored and
processed/rendered by a separate updateNodes function
  updateNodes(g, d.nodes) //g is the svg element and d.nodes the node
entries in each column group
  })
  // mouse event listeners are attached to the g. By dragging the svg g all
nested elements will be affected automatically
  .call(d3.drag( )
  .on("start", (event, d) {
  //set start properties
  })
  .on("drag", (event, d) {
  //handle drag properties and update column positions
  })
  .on("end", (event, d) {
  //update drag properties, update column positions, callback to update
modelHandler
  }]
```

-continued

```
Function updateNodes(__g, nodes) {
//select the svg elements and bind the nodes data
let gNode__g.selectAll('gNode').data(nodes);
gNode.enter( ).append('g')
.attr(id, gNode)
//iterate on each data element and append the visual elements like
rectangle, label etc. stored in d
.each(d => {
let g=d3.select(this)
g.append(rectangle).attr(width, d.width).attr(height, d.height).attr(fill,
d.color) ..... g.append(text).attr(x, d.x+12). attr(y, d.height/2).text('d.label)
})
//mouse event listeners
.on(mouseOver, (event, d) { activate Tooltip(d) })
.on(mouseMove, (event, d) { transitionTooltip(d) })
.on(mouseOut, (event, d) { removeTooltip(d) })
.on(click, (event, d) {filter callback to update modelHandler })
}
```

As explained above, the Component View Handler 32 comprises functionality for user interactions, including column drag and drop, and column reposition and removal. With respect to repositioning, the drag and drop functionality comprises three (3) steps. First, there is a start step, where the drag and drop mechanism is activated. Second, there is drag functionality, where in one embodiment, only visual objects in the browser (svg domain elements) are repositioned. The third step is the end, where updates are implemented to the relationPath and a callback to the controller.configHandler is performed that updates the underlying viewDataModel. Example pseudo code is described below with regard to the drag and drop/repositioning functionality:

```
    //Each column is associated with a d3 mouse event listener for the drag and
drop mechanism
    .call(d3.drag( )
    .on("start", (event, d) {
    // get and set start properties
    // event callback contains position properties of the mouse interactions
    // d = data element (node) bound to the column = to the source node in
    nodesIdMap
    variable column = d3.select(this) //select the active svg dom element
    column.raise( ) //overlay the column on top of the svg dom
  })
    .on("drag", (event, d) {
    // handle drag properties and update column positions (see drag start for
    properties)
    // Event is called on every mouse move after drag start
    columnIndex=d.index; // get current position index
    // select and iterate all columns to compare current x-position to x-position of
    connected columns left:columnIndex-1, right:columnIndex+1
    gColumns.selectAll(gColumn) // iterative list of all svg columns containing
    the data elements and properties
  // store index positions of the columns in case of re-ordering left - right if(
  event.x < gColumns[columnIndex-1] ) {
      d.index =-1; // change the index of the active column minus 1
      gColumns[columnIndex-1].index++; //add 1 to the index of the column to
      the left
    }else if ( event.x < gColumns[columnIndex+1] ) {
      d.index=+1; // add 1 to the index of the active column
      gColumns[columnIndex+1].index--; //subtract 1 to the index of the
      column to the right
    }
    // check if dragged column is out of range/overlaying the bin for removal
    if(event.x > svg.bin.attr(x) ) svg.bin.color('orange) //highlight the bin for
    notification of removal
    // reposition all columns based on their (new)index;
    gColumns.each(column   =>{
      if(column.index !== columnIndex) column.attr(x, column.index*width)
      //reposition the not active columns to the new index
      else if( column.index === columnIndex) column.attr(x, event.x) //reposition
      the active column to the mouse event properties
    })
```

-continued

```
    })
    .on("end", (event, d) {
      // Create a new ordered list
      // reposition all columns based on their (new)index and create a new ordered
      relationPath;
      variable newRelationPath *=[ ];
      gColumns.each(column =>{
      column.attr(x, column.index*width) //reposition the columns to the new index
        // check position for removal candidate, if so do not add the column to the
        new list
        if( column.attr(x) < svg.bin.attr(x) ) relationPath[index] =
        column.endpoint; //add endpoint to the newRelationPath
      })
      // the newRelationPath is passed to the controller.configHandler. See the
      component controllers for the functionalities.
      controller.configHandler(newRelationPath, false) //false is a flag that no new
      columns are added. This functionality is controlled by a separate HTML
      dropdown element.
    })
  )
}
```

As an illustration of the newRelationPath, the following example shows the situation before drag and drop, and after drag and drop of column 3 and column 1 (using the fruits example from TABLE 1) and a switched index in the order. For instance, before drag and drop, the relationPath is as follows:

```
relationPath":[
{endPoint: Column 1 (Fruits), orderBy: {sourceKey, ascending},
fiterProps:null},
{endPoint: Column 3, orderBy: {sourceKey, descending},
fiterProps:null},
{endPoint: Column 2, aggregateBy: { endpoint: column x,
fiterProps:null},
{endPoint: Column 4, fiterProps:null},
{endPoint: Column x, fiterProps:null}
],
  After drag and drop, the newRelationPath is as follows:
"newRelationPath":[
{endPoint: Column 3, orderBy: {sourceKey, descending},
fiterProps:null},
{endPoint: Column 1 (Fruits), orderBy: {sourceKey, ascending},
fiterProps:null}
{endPoint: Column 2, aggregateBy: { endpoint: column x,
fiterProps:null},
{endPoint: Column 4, fiterProps:null},
{endPoint: Column x, fiterProps:null}
],
```

Also as explained above, the Component View Handler 32 comprises functionality for user interactions that include adding columns. For instance, based on the config.availableEndpoints, an HTML dropdown list may be created in the view. This dropdown may be populated by the availableEndpoints list. By selecting one or more items in the dropdown list, a callback is performed to the controller.configHandler, which updates the configurations (as explained above with regard to the component controllers). An illustrative example of pseudo code for add functionality for the Component View Handler 32 is described as follows:

```
//dropdown is activated by clicking on the config icon
// A list with additional endpoints/columns is shown
// By selecting 1 or more items a list with endpoints is created
// By clicking apply the list is passed to the controller.configHandler( )
variable newEndPoints:[ ]
onSelectItem(item) newEndPoints.add(item) onDeSelectItem(item)
newEndPoints.remove(item)
```

-continued

```
Function applyNewEndPoints -> controller.configHandler(newEndPoints,
true)
//True is a flag to indicate new added endpoints
```

Additional functionality of the Component View Handler 32 comprises node filtering and tooltip handling. As to general node set up, within each gColumn, the svg nodes are nested. Each node comprises a group that contains an svg rectangle and a label. In one embodiment, the rectangle contains three mouse event listeners (as described for the patient flow chart rendering), including mouseOver (to activate the tooltip), mouseMove (to transition tooltips position to follow mouse movements), mouseOut (to de-activate the tooltip), and click (callback to the filterUpdateHandler). With respect to nodes filtering, the filtering is activated or de-activated by a mouse click on the node. Example pseudo code is as follows:

```
//The mouse click captures the node key and endpoint out of the data
element bound to the node (d) and does a callback to the filterHandler
in the component controller
gNode.on(click, (event, d) {
//callback to the controller with the nodes key and endpoint
controller.filterHandler(d.endpoint, d.key) //example
controller.filterUpdateHandler(Fruits, Apple)
})
```

For the tooltip handling, the tooltip is activated and de-activated by touching the node area with mouse movements (e.g., hover-over). The tooltip itself is an HTML/CSS element. The content is dynamically created in the mouse event callback and passes to the HTML element. The visibility of the tooltip is controlled by style sheet (CSS) class management. Example pseudo code is as follows:

```
//activate the tooltip
node.on(mouseOver, (event, d) { activateTooltip(d) }) function
activateTooltip(event, node){
//the HTML content may be freely generated based on the data entries,
descriptions, labels, etc. in the node data element
variable htmlContent; //text content in HTML markdown
htmlContent.header=node.header;
htmlContent.subHeader=node.subHeader+ +node.value+ +(node.ratio);
```

-continued

```
//if there is an aggregatedBy data object available in the node, it is
passed to a d3-Chart function in the tooltip class that generates a
horizontal bar chart.
if(node.aggregatedBy){
htmlContent.chart=toolTip.creatChart(node.aggregatedBy) //creates
the nested horizontal chart
}
toolTip.html=htmlContent; //inserts the html content
toolTip.attr(visibility, visible) //css property
transitionTooltip(event, d) //sets the correct position sync with the
mouse position
}
//controls the tooltips position based on the mouse events properties
(event.x, event.y)
node.on(mouseMove, (event, d) { transitionTooltip(event) })
function transitionTooltip(event){
toolTip.attr(x, event.x)
toolTip.attr(y, event.y)
}
//de-activates the tooltip by setting the css attr visibility
node.on(mouseMove, (event, d) { transitionTooltip(event) })
function transitionTooltip(event){
toolTip.attr(visibility, hidden)
}
```

In one embodiment, the interactive flow diagram generation system 18 (and the interactive flow diagrams it generates) can be a new feature added to existing analytics applications, embedded inside the ISPM platform (e.g. via an insights tab in the lung cancer orchestrator). In some embodiments, the interactive flow diagram generation system 18 may serve as a new feature added to other patient management applications, extracting and visualizing data extracted from those applications. In some embodiments, the interactive flow diagram generation system 18 may be added as a feature to other existing analytics solutions, such as Philips PerformanceBridge. In some embodiments, the interactive flow diagram generation system 18 may be a standalone application, which may be provided to any customer that is maintaining spreadsheets or a database with information on their patient cohorts and wishes to gain insights from it in an interactive way. In some embodiments, the interactive flow diagram generation system 18 may be offered along with a service, such as a clinical consulting/analyst/data design service for connecting the flow visualization application to hospital spread sheets and deriving the insights from them.

Figure 3A:
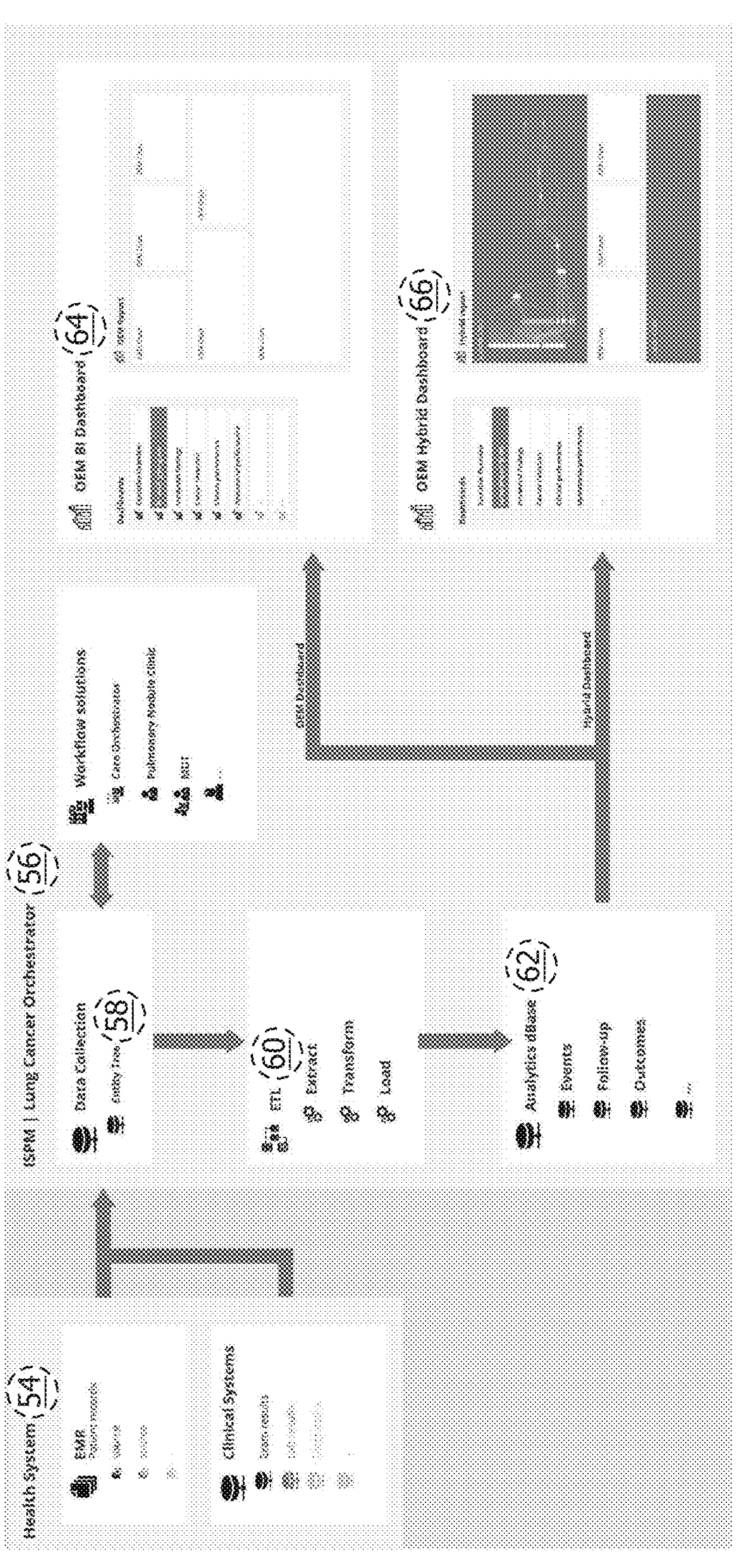
FIG. 3A is a schematic diagram that illustrates an embodiment of an example interactive flow diagram generation system embedded in an analytics context, in accordance with an embodiment of the invention.

FIG. 3A is a schematic diagram that illustrates an embodiment of an example interactive flow diagram generation system embedded in an analytics context. Shown is a health system 54 and an ISPM-based lung cancer orchestrator 56. The health system 54 comprises a health information management system (e.g., electronic medical records (EMR), clinical system records, etc.). Data is extracted from the health system 54 (e.g., from an information management system) and into the Intellispace Precision Medicine (ISPM) platform, which comprises a dedicated patient management application such as a care orchestrator (e.g., Lung Cancer Orchestrator 56). In the ISPM platform, the data are stored in a relational data model called an entity tree 58. The data are extracted using Extract Transform and Load (ETL) pipelines 60 and stored in an analytics database 62. The data from the analytics database 62 get displayed in analytics dashboards, which can comprise both standard charts 64 and custom charts 66. In one embodiment, an interactive flow diagram may be provided as a custom chart to the existing analytics context, in a hybrid model, in which it can interface (e.g., send/receive information) with other business intelligence (BI) frameworks, utilizing software libraries.

Figure 3B:
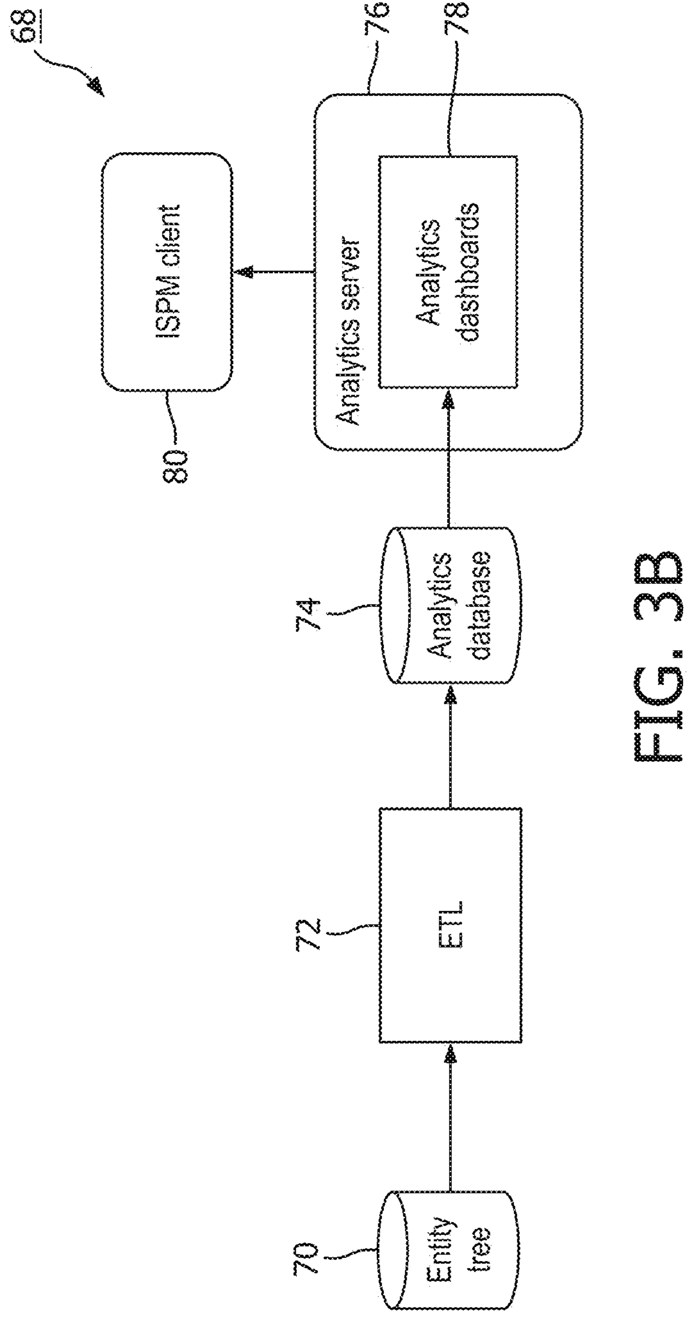
FIG. 3B is a schematic diagram that illustrates an embodiment of a high level architecture of an analytics application, in accordance with an embodiment of the invention.

Digressing briefly, and referring to FIG. 3B, shown is an example high level architecture of an analytics application 68 (e.g., which may correspond to elements within or associated with ISPM-based lung orchestrator 56 in FIG. 3A). In one embodiment, the analytics application 68 comprises an ISPM entity tree 70, an ETL (NiFi ETL) pipeline 72, an analytics database 74, an analytics server 76 comprising analytics dashboards 78, and an ISPM client 80. Note that in some embodiments, the analytics application 68 comprises fewer (or more) than the functionality depicted in FIG. 3B. Briefly, the analytics application 68 comprises a software feature configured in one embodiment as an embedded analytics application on the ISPM platform.

The ISPM entity tree 70 comprises data captured while creating and executing workflows (e.g., actions taken by a user of the patient management application while navigating through patient care steps, including populating fields with patient data in several display user interfaces, ordering, scheduling exams, collecting data, etc.) in ISPM and the results captured while executing these workflows.

The ETL pipeline 72 extracts data from the ISPM entity tree 70, transforms it into a format suitable for analytics, and loads it into the analytics database 74. The ETL pipeline 72 comprises three steps: (1) Extract: fetch objects from the entity tree 70; (2) Transform: create NiFi FlowFile attributes from these objects; and (3) Load: insert records filled with these attributes into the analytics database 74. Note that the objects themselves are defined in the entity tree 70. The objects that are fetched are described in the NiFi pipeline. In other words, the objects are not defined in the NiFi pipeline, but are used in the pipeline to describe analytical behaviors associated to it and therein named as attributes. Additionally, the transformation is from the data in the lung nodule management program to a format suitable for populating the database structures of the analytics database. It should be appreciated by one having ordinary skill in the art that there may be some additional cleaning and normalization performed.

The analytics database 74 comprises the data as extracted from the ISPM platform in a format suitable to build the analytics dashboards 78.

The analytics dashboards 78 are built on top of the analytics database 74 and provide end-user insights.

The ISPM client 80 makes the analytics dashboards 78 available to an end-user(s) via embedded analytics pages in the ISPM.

Figure 4A:
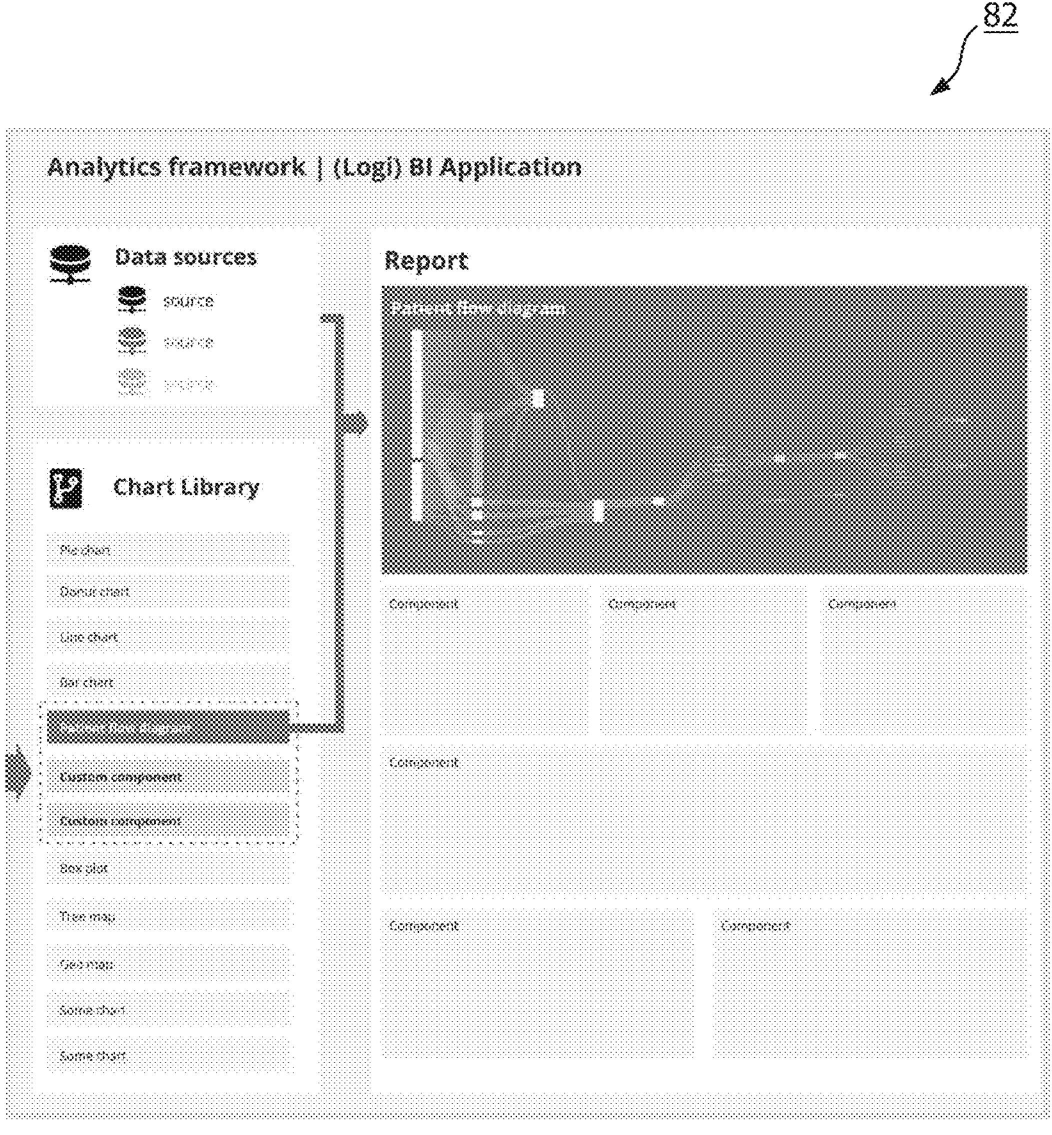
FIGS. 4A-4B are schematic diagrams that illustrate an embodiment of an example interactive flow diagram generation system embedded in example analytics contexts, in accordance with an embodiment of the invention.
Figure 4B:
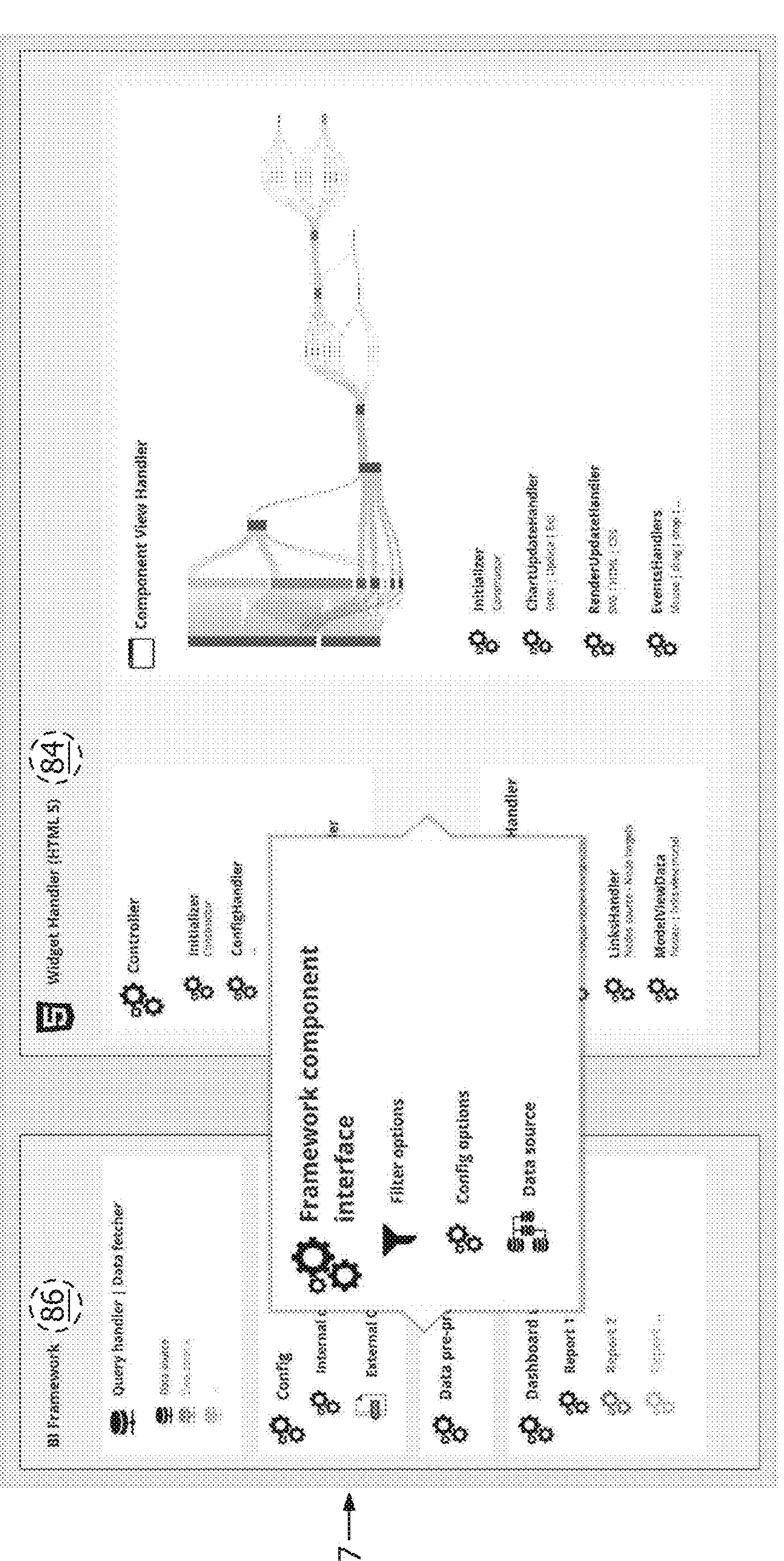

Continuing with example integrations of the interactive flow diagram generation system in various platforms, FIGS. 4A-4B are schematic diagrams that further illustrate an embodiment of an example interactive flow diagram generation system embedded in example analytics contexts. For instance, FIG. 4A shows an analytics framework 82 where the interactive patient flow diagram (e.g., interactive flow diagram) may be added as a custom chart (e.g., in the chart library).

FIG. 4B illustrates how a patient flow widget handler 84 (e.g., in HTML) can interface with an existing Business Intelligence (BI) framework 86 utilizing the query handler and data pre-processor 87 of the BI framework 86. The widget handler 84 comprises a wrapper around the component, and resides in the external BI framework 86 and is framework dependent. The patient flow visualization component itself is framework agnostic.

In view of the above description, several features of and/or involving the implementation of certain embodiments of an interactive flow diagram generation system 18 are noteworthy. In general, an interactive flow diagram displays data from one or a combination of data sources (e.g., from one or more spreadsheets and/or an analytics database). The data for certain embodiments of an interactive flow diagram are contained in the data source (e.g., data source 26, FIG. 2A), including an analytics SQL database. The data may be extracted from, for instance, the lung cancer orchestrator using ETL pipelines. In some embodiments, the data model and interactive flow diagram may be connected to any data source (e.g., flat excel spread sheets, SQL data bases, etc.). The data may be automatically extracted from the patient management application (e.g., via extract, transform, and load (ETL) pipelines as described above). As part of the data extraction, patient demographic and patient details information from the patient management application (e.g., lung cancer orchestrator) are automatically aggregated. With reference to FIG. 2A, the Component Controller 28 loads the default configuration and initiates the default view of the interactive flow diagram, utilizing the Component Model Handler 30 (nodesHandler 42 and linksHandler 44) to generate a unique list of nodes and links as described above.

Figure 5:
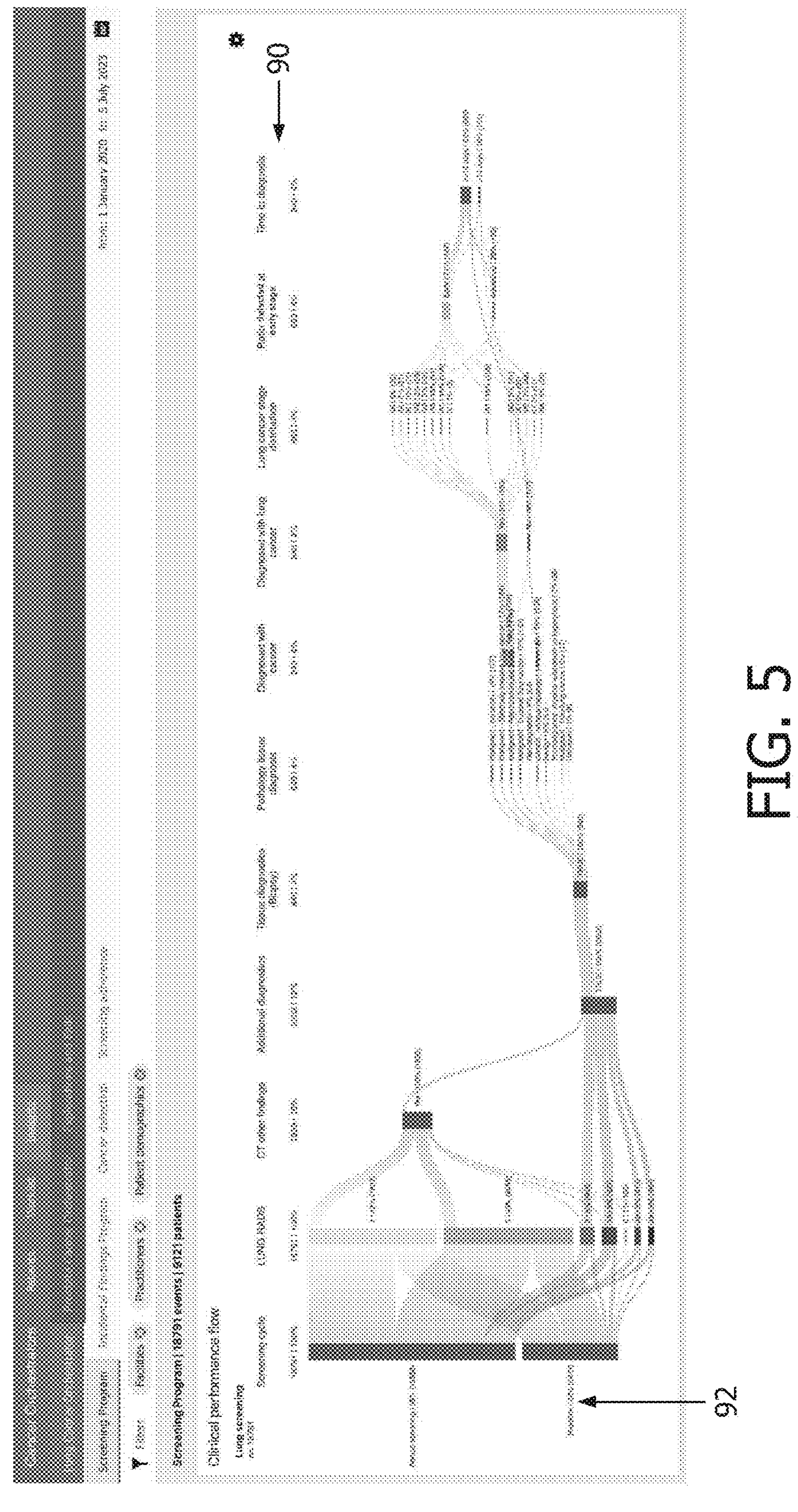
FIG. 5 is a screen diagram that illustrates an embodiment of an example interactive flow diagram embedded in a lung cancer orchestrator, in accordance with an embodiment of the invention.

A modelView is created and displayed as an interactive flow diagram 88 in FIG. 5 as part of functionality of the lung cancer orchestrator (e.g., here showed as part of the screening program of the existing Philips lung cancer orchestrator). In other words, in the depicted embodiment, the interactive flow diagram 88 is embedded in a lung cancer orchestrator. As shown in FIG. 5, the columns 90 correspond to lung screening features (with value|ratio beneath each column heading) as an illustrative example, including (from left to right) screening cycles (Baseline/Annual), Lung-RADS scores, cycles with CT other findings, cycles with additional diagnostics, cycles with tissue diagnostics/biopsy, cycles with pathology tissue diagnosis, number and percentage diagnosed with cancer, number and percentage diagnosed with lung cancer, lung cancer stage distribution, and ratio detected at early stage. The nodes 92 comprise two categories (with ratio (value) adjacent each category), including annual screening and baseline. Though a reference line refers to one of the nodes, it is noted that the nodes are distributed throughout the interactive flow diagram 88. Note that in some embodiments, the interactive flow diagram 88 provides the user with an ability to visualize, or not visualize, blanks or voids in the data.

In some embodiments, the interactive flow diagram generation system 18, through implementation of the interactive flow diagram 88 (as assumed throughout the disclosure), provides the user with the ability to add customized clinical rules (e.g., define group values inside a data category and show the groups in the interactive flow diagram 88 rather than the individual values). For example, the user may be provided the ability to group all cancer stages into early and advanced stages, and show only the amount and percentage of early stage vs advanced stage cancers. In one embodiment, customized clinical rules may be added via the model handler, or in some embodiments, the user may add such a rule via specification in a configuration window that updates the configuration file. Referring to FIG. 5 for an illustrative example, for the columns 90 corresponding to Lung cancer stage distribution and Ratio Detected at early stage, a customized clinical rule may define which stages should be considered as Early. For instance, in one embodiment, the rule set is described in the configuration file, and a user may access the configuration menu where the user can add a new column (e.g., ratio detected at an early stage) that may be based on an existing column (e.g., lung cancer stage distribution), specify that the new column consists of two main nodes (e.g., early stage and advanced stage), and further specify which stage values belong to which node.

Figure 6:
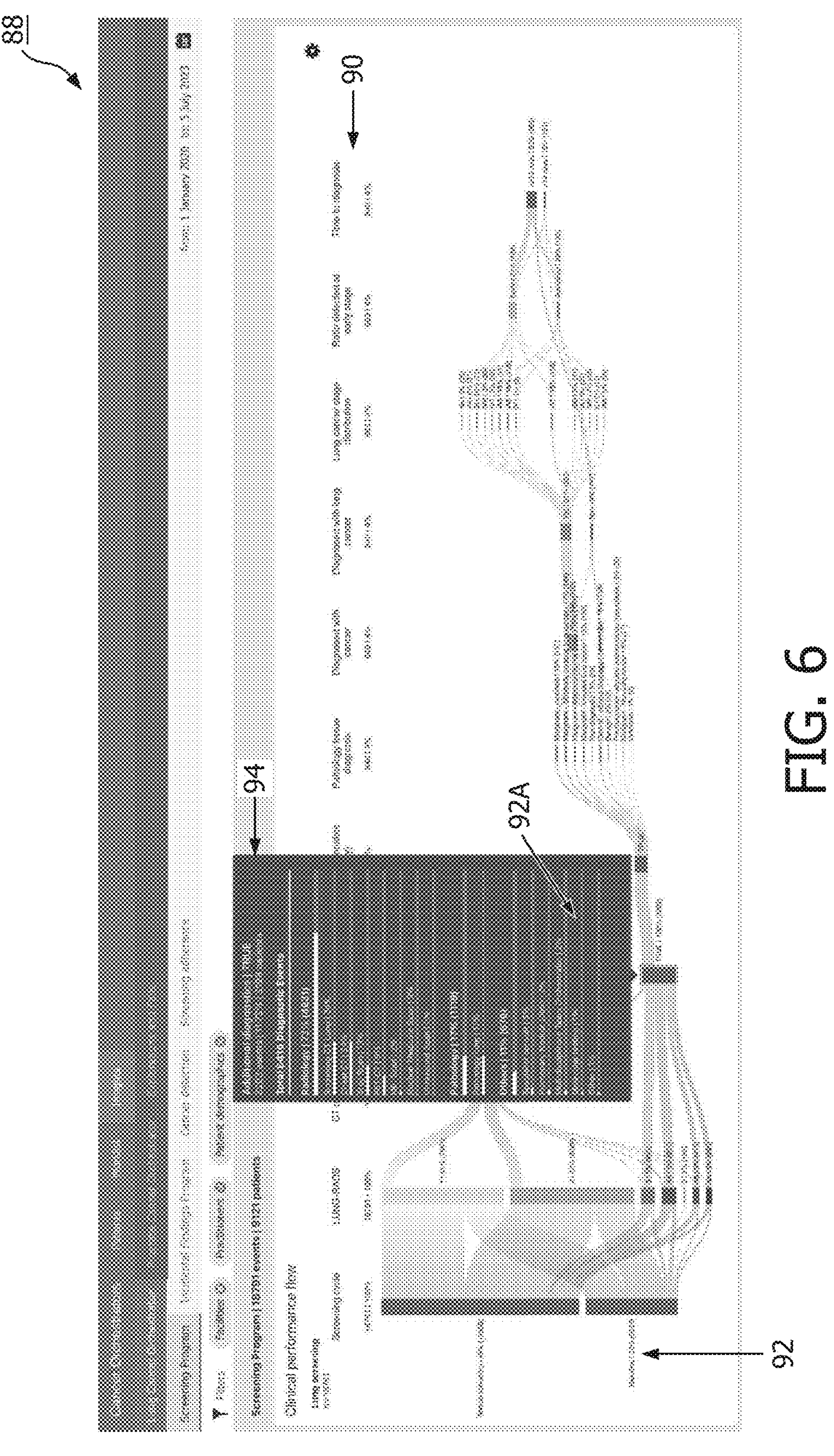
FIG. 6 is a screen diagram that illustrates an embodiment of an example interactive flow diagram presenting details of aggregated metrics based on hover-over functionality, in accordance with an embodiment of the invention.

FIG. 6 shows the interactive flow diagram 88 of FIG. 5, with details of aggregated metrics based on hover-over functionality with an input device. As depicted in FIG. 6, the interactive flow diagram 88 includes an aggregated information component 94 that is prompted by user interaction with the interactive flow diagram 88. For instance, the user may manipulate an input device (e.g., mouse) over one of the nodes 92, and by merely hovering (e.g., no mouse click, though some embodiments may use actual mouse left or right button selection) over the desired node, more details of aggregated information for the node is displayed via the aggregated information component 94. In this example, the user has hovered a mouse over the True node 92A to view more details of aggregated information for patients that received diagnostic testing. Upon a hover-over action, a breakdown of the diagnostic tests is displayed (e.g., showing radiology, screening CT lung, chest CT, Xray scan, etc., as well as pathology and other diagnostics including specialist consultation, pulmonary nodule clinic, etc., with associated value|ratios). In one embodiment, a ToolTipHandler determines, based on the data structure, if the ToolTipHandler displays a text element or graphical data presentation/visualization upon mouse (or other input) interaction. The ToolTipHandler interrogates the node (e.g., node 92A) to determine if there is an 'Aggregated by' object (as defined in the aggregation information in the config file 24, FIG. 2A) that can be displayed in the mouse tooltip.

Figure 7:
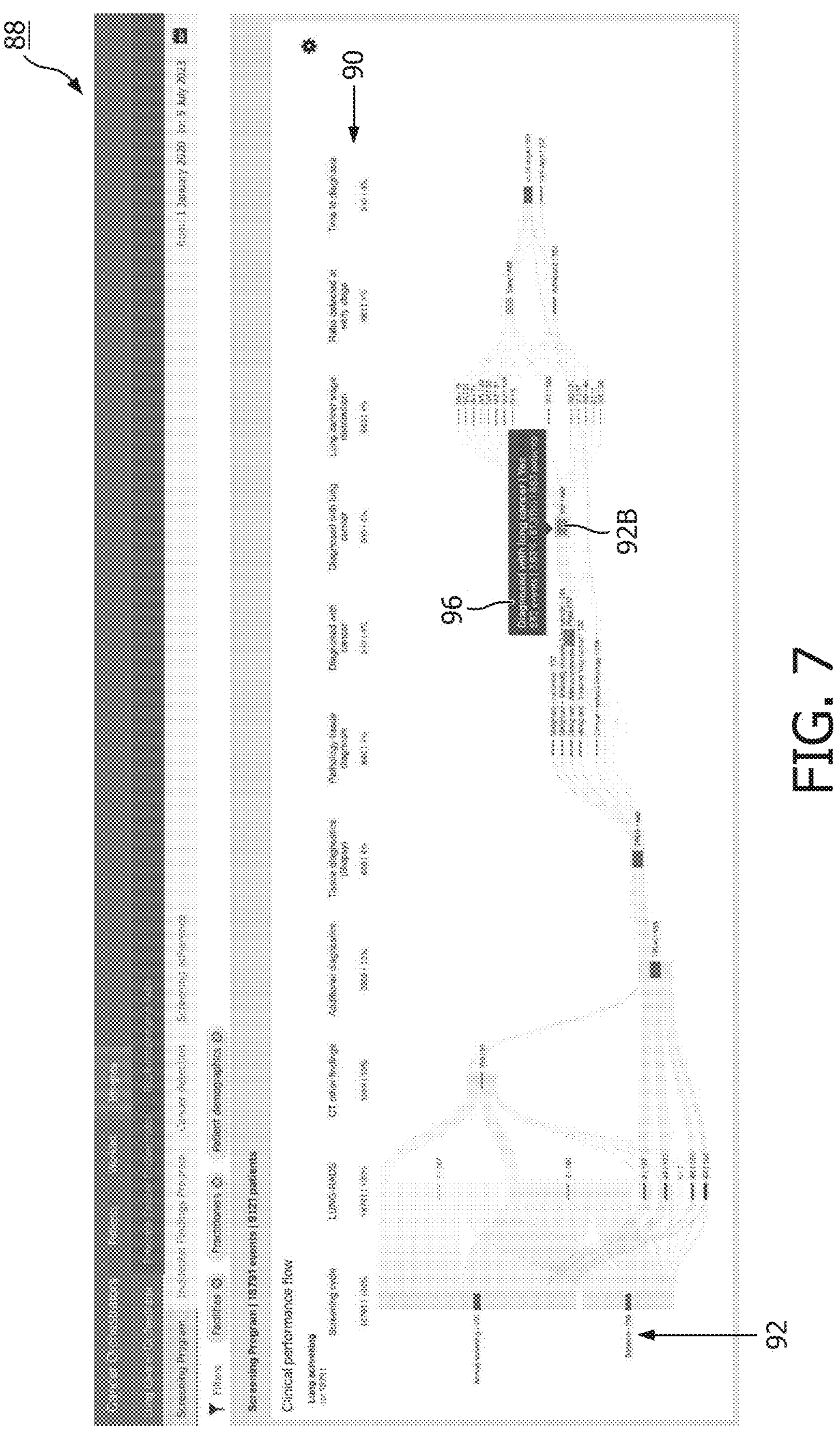
FIG. 7 is a screen diagram that illustrates an embodiment of the example interactive flow diagram isolating sub-population information based on user interaction with a portion of the interactive flow diagram, in accordance with an embodiment of the invention.

FIG. 7 illustrates an embodiment of the example interactive flow diagram 88 isolating the flow of selected sub-population information based on user interaction with a portion of the interactive flow diagram 88. In this example, the user maneuvers the input device (e.g., mouse) over the "yes|683" node 92B under the column 90 labeled diagnosed with lung cancer. Upon mouse interaction (e.g., left or right click, or hover-over functionality), a sub-population component 96 (e.g., showing in this example information including sub-populations diagnosed with lung cancer, with metrics including 683 events|3.63% (81.31%)|683 patients) is displayed. In this manner, the user is provided the ability to isolate the flow of one of the sub-populations. For instance, the user may isolate the flows of the patients diagnosed with lung cancer. The interactive flow diagram generation system selects only subpopulations of patients diagnosed with lung cancer, and shows only nodes and flows of this subset of patients, while highlighting or emphasizing in the other columns only the part of the nodes belonging to this subset of patients and displaying only the flows of this subset. Thus, the sub-population component 96 merely shows which node has been selected, and responsive to the selection, the nodes and flows of the sub-population or subset are emphasized (e.g., shown with darker colors) and those not part of the sub-population de-emphasized (e.g., shown with lighter colors). Note that FIG. 6, on the other hand, is merely illustrating how more details of a node may be shown. In one embodiment, the Component Model Handler 30 (FIG. 2A) returns a derived model that is a subset of the full model, based on the selected node. The Component Model Handler 30 evaluates which sub-population is represented in the selected node and isolates the flows and (part of the) nodes that are associated with it in the manner as described above in association with FIG. 2A.

Figure 8:
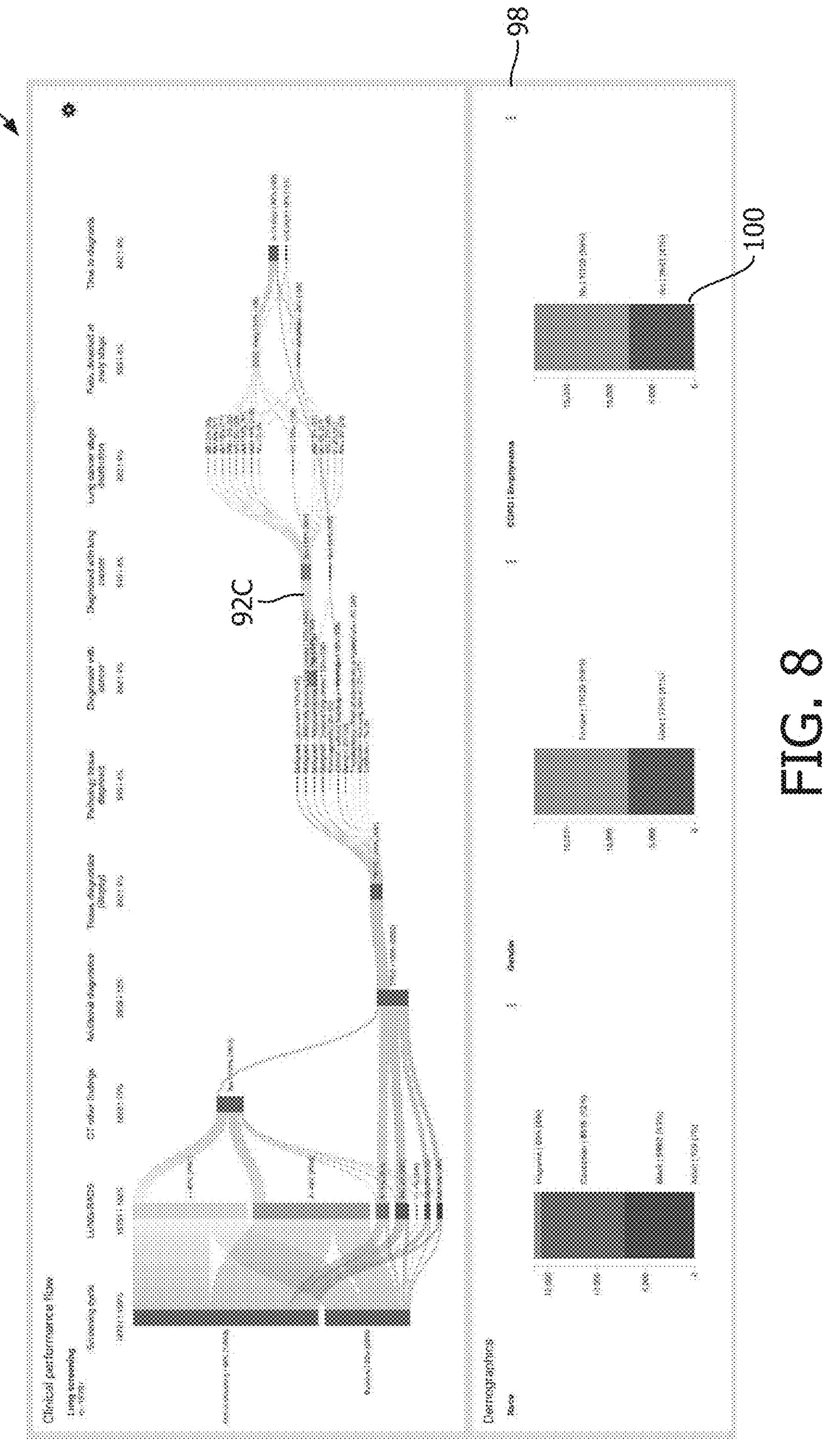
FIG. 8 is a screen diagram that illustrates an embodiment of the example interactive flow diagram serving as a navigational model for connected graphs that present patient demographic information, in accordance with an embodiment of the invention.

FIG. 8 illustrates an embodiment of the example interactive flow diagram 88 serving as a navigational model for connected graphs that present patient demographic information. In other words, the interactive flow diagram generation system 18 enables the user to use the interactive flow diagram 88 to break down or drill down into characteristics of sub-populations in connected graphs. For instance, upon selection of a node 92C, a demographics panel 98 is presented (in this example, beneath the interactive flow diagram 88, though not limited as such), displaying within the demographics panel 98 graphs or charts 100 (e.g., in this example, respective charts showing breakdowns for race, gender and COPD|Emphysema (yes/no)) (e.g., shown in the bar chart in the bottom right) of demographics of the selected sub-population. By clicking on nodes in the flow diagram 88, various characteristics of the selected population (e.g., the presence of emphysema) are displayed in the charts adjacent the flow diagram 88. Such information may be displayed, in some embodiments, in the flow diagram, yet not considered a main data category (and hence not omitted from the patient flow overview). The invoking of this information may be triggered based on any one of a plurality of different user interactions. For instance, for isolation, the user may right-click using a mouse and invoke the demographics of a sub-population using the left mouse click. However, it should be appreciated that there are a multitude of user interactions that may be used in some embodiments (as is true with other user interactions described herein with the flow diagram 88). For instance, a mouse click may prompt a pop-up menu that appears, within which the user may select the next action(s) to be triggered (e.g., filter, isolate, show demographics, etc.) In one embodiment, and as explained above, the FilterHandler 38 of the Component Controller 28 (FIG. 2A) tracks which filter has been applied (e.g., through user interaction), and a new model is generated (in combination with the configuration) based on the selected node 92C. The FilterHandler 38 also parses the information to the BI framework, and in particular, to the root of the report where the source data is described (there, the same filter is applied, such that connected graphs are also filtered).

Figure 9A:
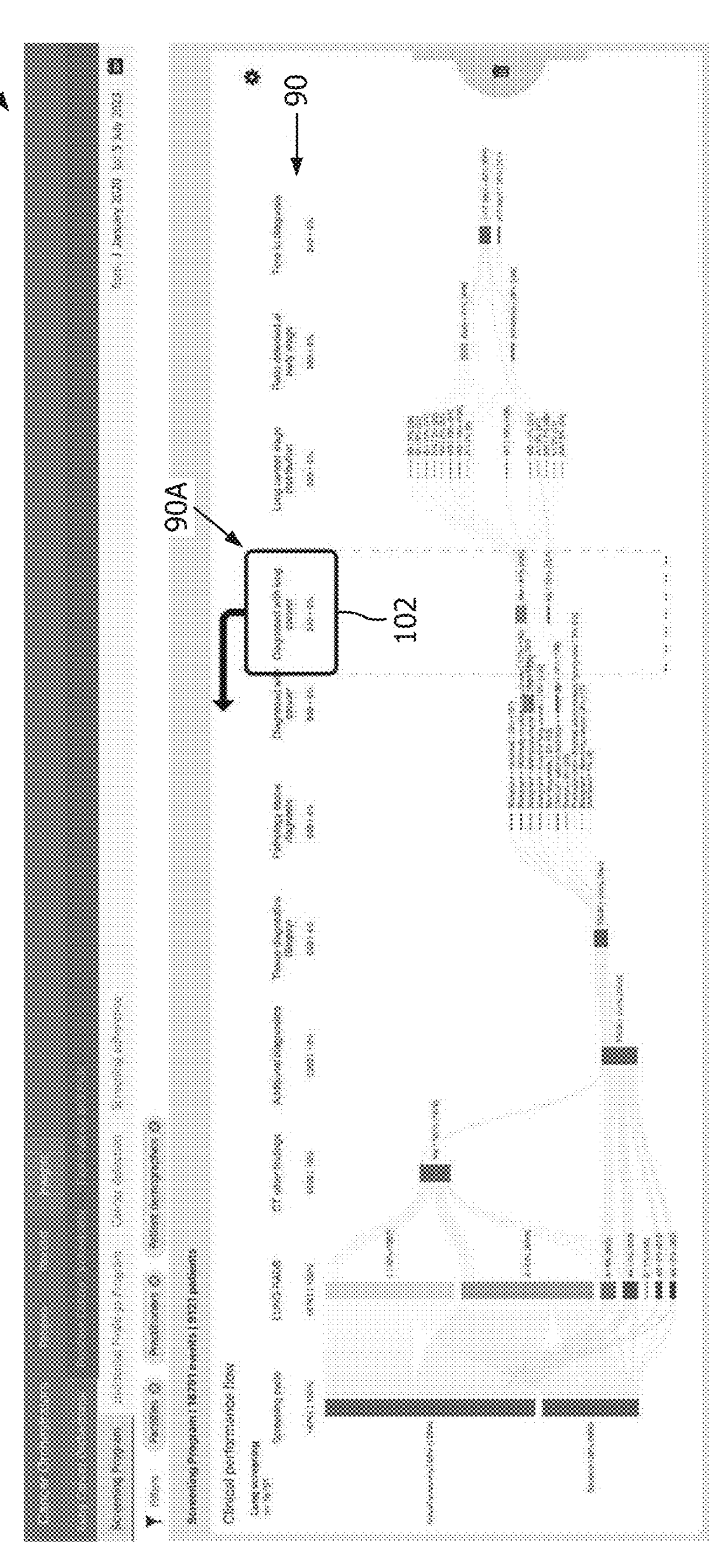
FIGS. 9A-9B are screen diagrams that illustrate an embodiment of the example interactive flow diagram enabling interactive drag and drop functionality, in accordance with an embodiment of the invention.
Figure 9B:
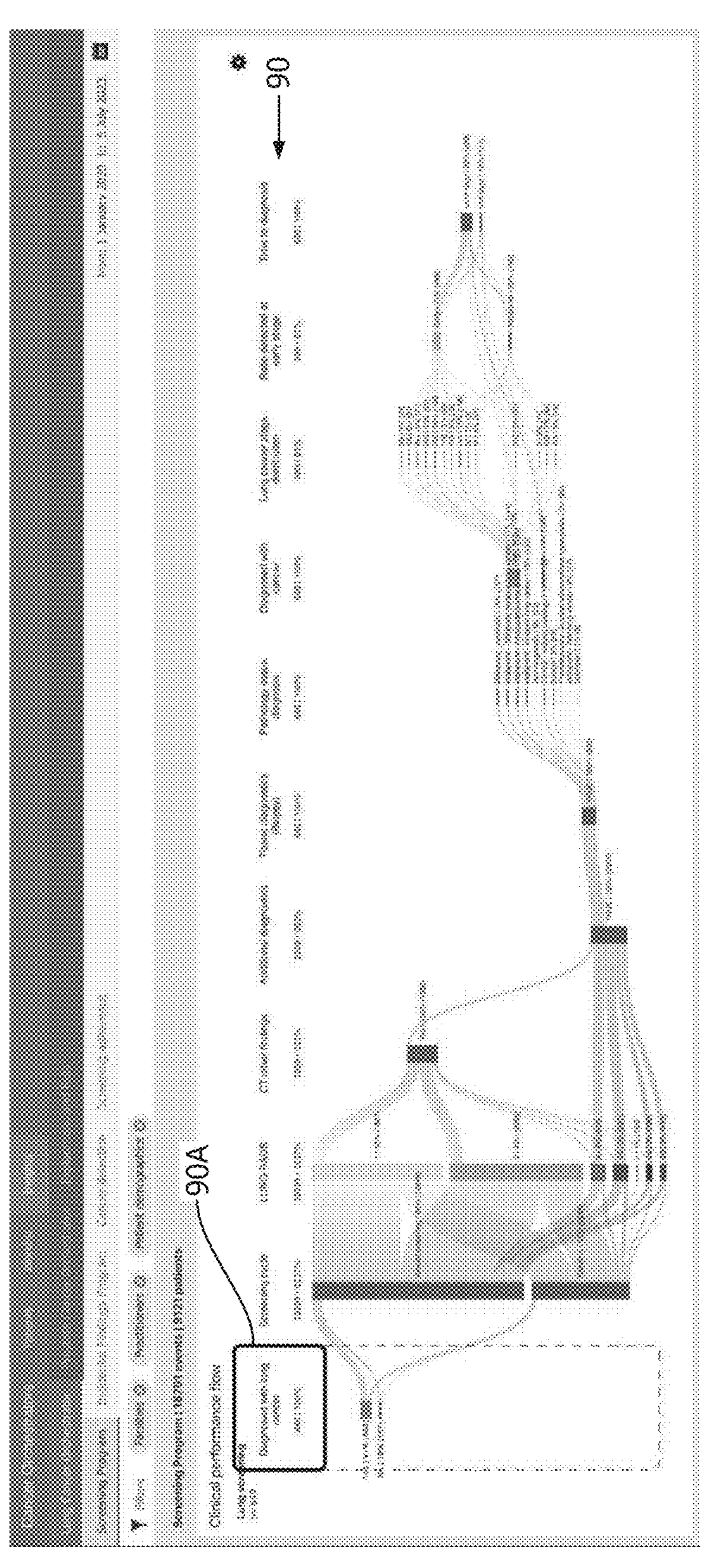

FIGS. 9A-9B illustrate an embodiment of the example interactive flow diagram 88 enabling interactive drag and drop functionality. The drag and drop functionality provides the user the ability to dynamically alter the order of values (e.g., columns) in the interactive flow diagram 88, which dynamically updates the data model and the interactive flow diagram 88. The drag-and-drop functionality is symbolically (i.e., not in actual implementation, though in some embodiments, may be visually distinguished to indicate this action) represented using the arrowed box 102 around the diagnosed with lung cancer column 90A in FIG. 9A, and reflects the mechanism of the interactive flow diagram 88 in enabling a user the ability to drag-and-drop columns 90 (e.g., here, 90A), dynamically altering the column positions through user interactions. This column drag-and-drop feature provides the user the ability to inspect the data from a different perspective. Referring to FIG. 9A, whereas the flow (e.g., from left to right) provided by the interactive flow diagram 88 is visualized in chronological order (e.g., from the patient's first scan or screening exam until the lung cancer diagnosis), in FIG. 9B, the flow starts with whether there was a lung cancer diagnosis or not (i.e., the diagnosed with lung cancer column 90A now at the left-most side of the interactive flow diagram 88). Based on this re-positioning, the user can observe of all patients with a lung cancer diagnosis via which flow (i.e., via which sequence of events) were these lung cancers found. In other words, the user is provided the ability to visualize via which path the lung cancer cases were identified. In one embodiment for implementing this type of interaction with the interactive flow diagram 88, and with reference also to FIG. 2A and described above, the Component View Handler 32 responds to the mouse interaction (drag-drop) and informs the ConfigHandler 36 that columns have been repositioned. The StateUpdateHandler 40 of the Component Controller 28 updates the model based on the repositioned columns and the Component Model Handler 30 creates a new ModelView based on the new structure of nodes and links. The Component View Handler 32 renders the new chart or diagram 88.

Figure 10A:
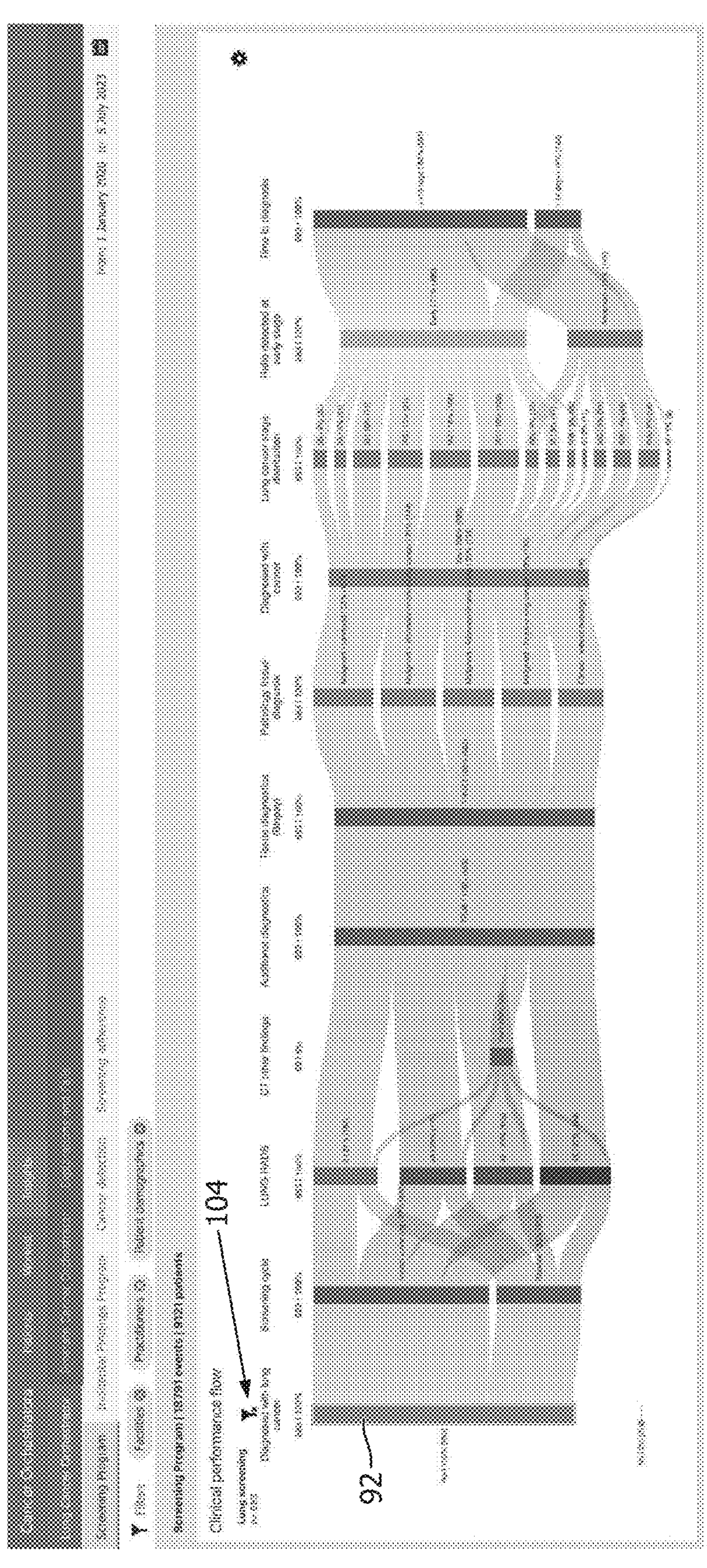
FIG. 10A is a screen diagram that illustrates an embodiment of the example interactive flow diagram enabling user-invoked filtering of flows and graphs by sub-population, in accordance with an embodiment of the invention.
Figure 10B:
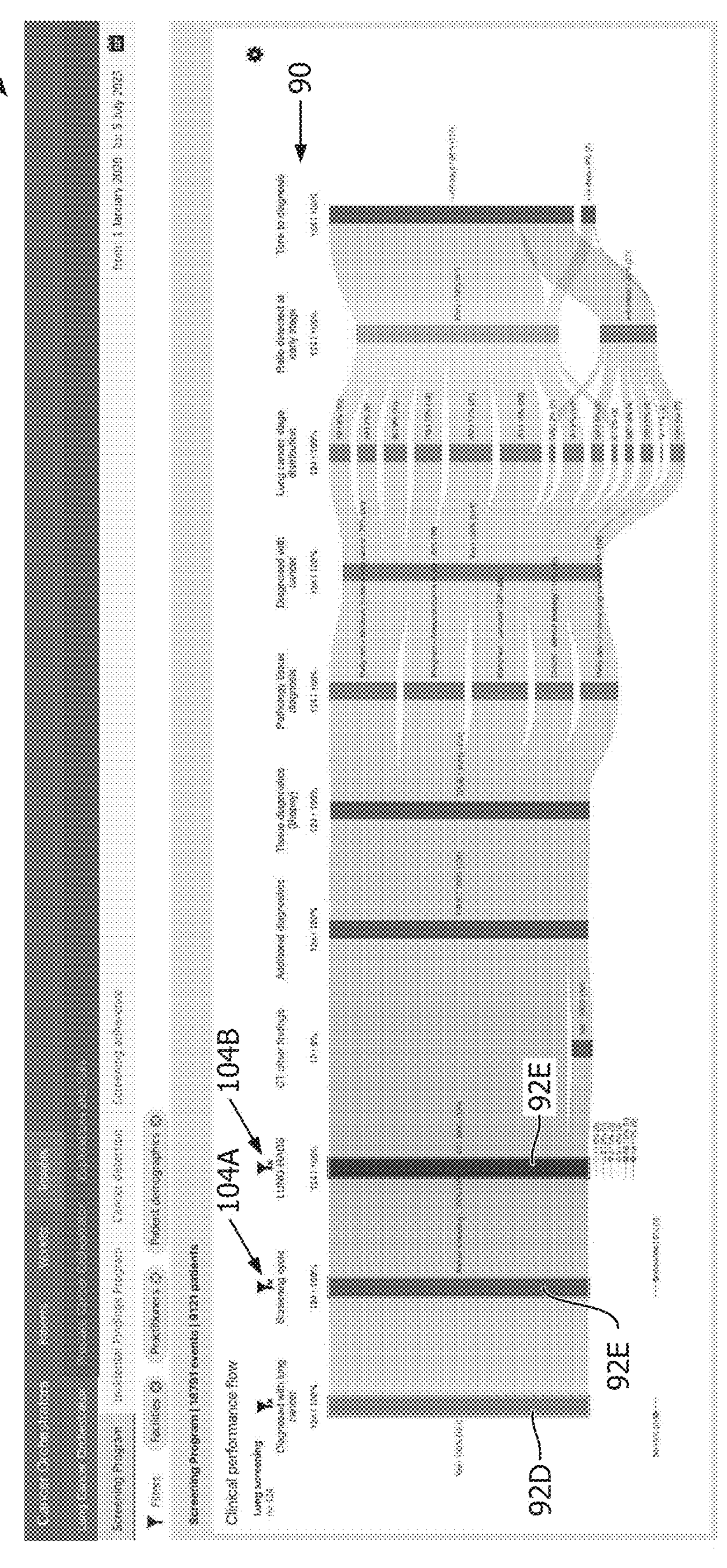
FIG. 10B is a screen diagram that illustrates an embodiment of the example interactive flow diagram enabling additional filters and filtered nodes, in accordance with an embodiment of the invention.
Figure 10C:
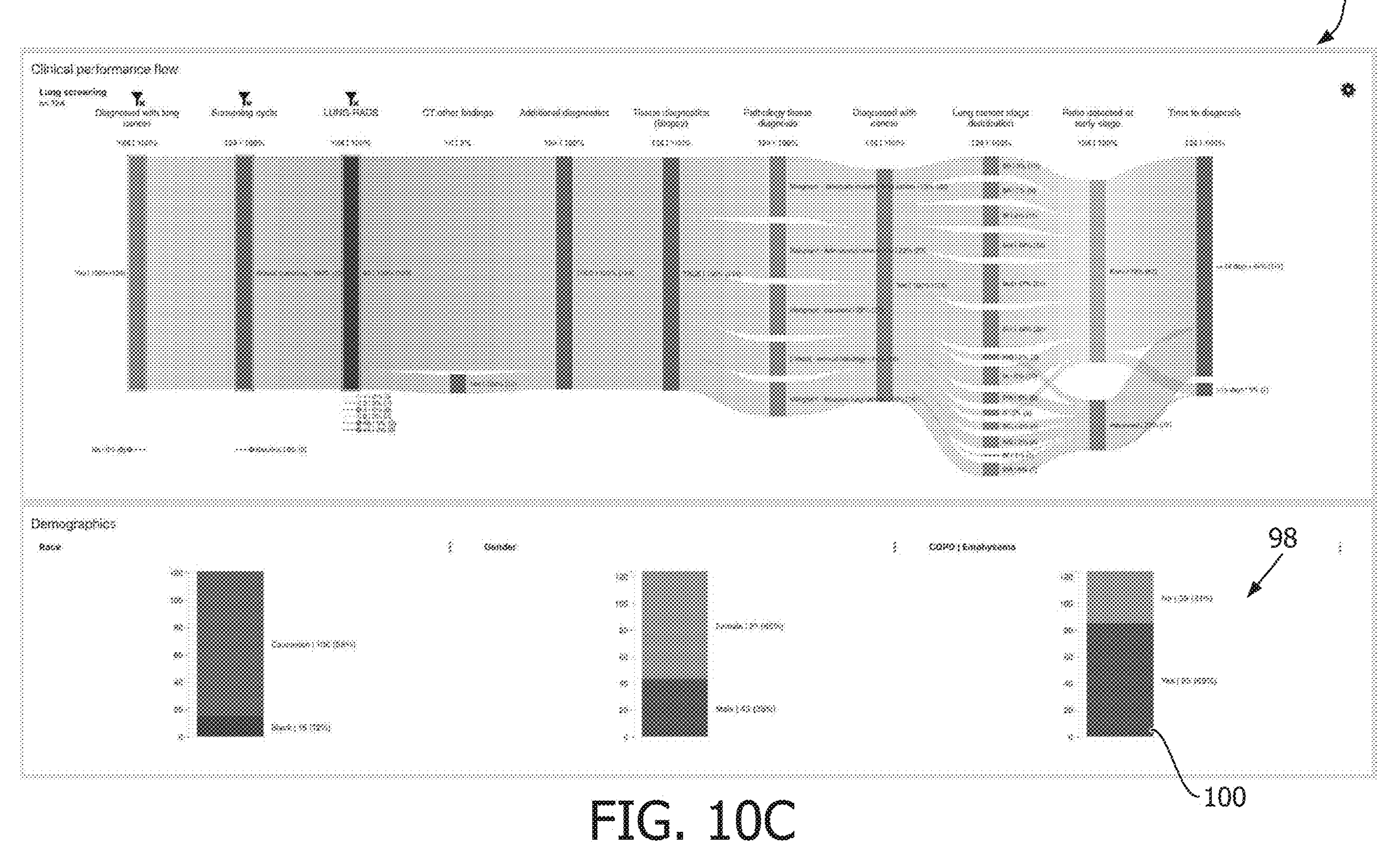
FIG. 10C is a screen diagram that illustrates an embodiment of the example interactive flow diagram enabling views of demographic information of sub-populations selected via filters, in accordance with an embodiment of the invention.

FIGS. 10A-10C illustrate example filtering functionality on the column-repositioned interactive flow diagram 88 (e.g., of FIG. 9B). Referring to FIG. 10A, the interactive flow diagram 88 illustrates user-invoked filtering (e.g., via a single click of a mouse on one of the nodes) of a single node. In general, by the user selecting a specific node, only nodes and flows are shown of the patient from other columns that were also in the selected node. In other words, the other nodes and flows are filtered by the selected node. For instance, in this example, by the user selecting the node 92 under the column 90 corresponding to diagnosed with lung cancer, only patients with a lung cancer diagnosis are selected, as indicated to a user by a filtering icon 104 located above the node 92 and the expansion (e.g., vertically) of the node 92 (compared to the same node in FIG. 9B). As a result, the user can see via which flow (i.e., sequence of events) these lung cancers were found. In effect, the interactive flow diagram 88 provides the user the ability to dynamically add endpoints (e.g., columns) to the interactive flow diagram 88, which dynamically updates the data model and the interactive flow diagram 88.

To implement this interaction (including those described below for FIGS. 10B-10C), in one embodiment and referring also to FIG. 2A and as explained above, the Component View Handler 32 responds to the mouse interaction (filter) and informs the FilterHandler 38 that nodes have been filtered. The StateUpdateHandler 40 of the Component Controller 28 updates the model based on the filtered nodes and the Component Model Handler 30 creates a new ModelView based on the filtered nodes and links. The Component View Handler 32 renders the new diagram 88.

The filtering functionality is not limited to a single node (or selection of a single node). FIG. 10B shows the interactive flow diagram 88 and how the user can apply additional filters to filter based on selection of multiple nodes 92 in one or more columns 90 at the same time. In the depicted example, in addition to the filter for node 92D, nodes 92E corresponding to screening cycle and Lung-RADS score, as reflected by icons 104A and 104B, respectively, above the corresponding columns 90, are selected by the user for filtering.

FIG. 10C illustrates the interactive flow diagram 88 of FIG. 10B, with the addition of the demographics panel 98 with demographic graphs or charts 100. FIG. 10C shows how the connected graphs 100 (e.g., that display patient demographics as explained above) are updated based on the filters applied, such that characteristics of only the selected sub-population are shown. Note that use of the term, connected, is intended to illustrate that the data displayed in the graphs adjacent (e.g., under) the flow diagram 88 is updated based on interactions with the flow diagram. That is, interactions with the flow diagram drive what information is displayed in the other graphs.

Figure 11:
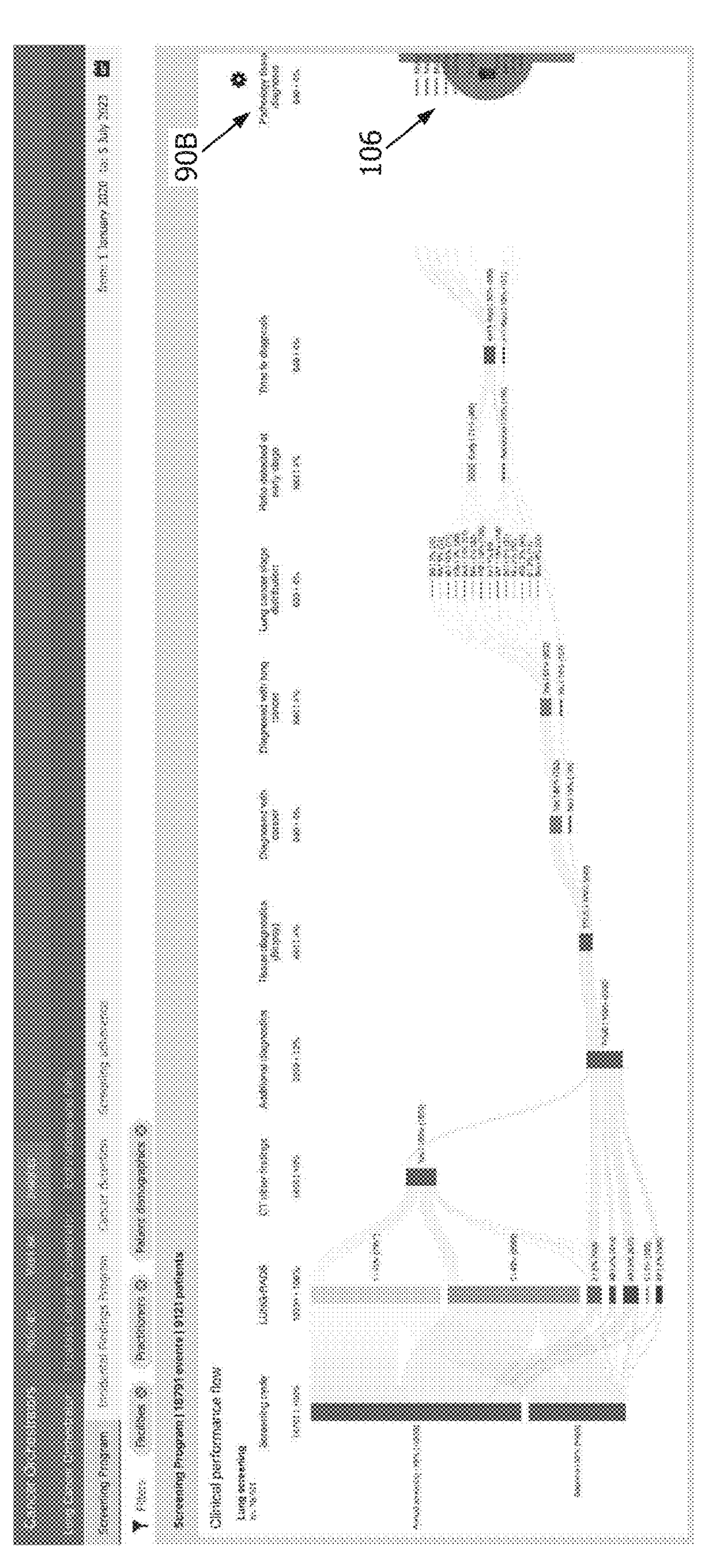
FIG. 11 is a screen diagram that illustrates an embodiment of an example interactive flow diagram enabling removal of columns, in accordance with an embodiment of the invention.

FIG. 11 shows the ability (of the user interacting with the interactive flow diagram 88) to remove columns 90 from the interactive flow diagram 88 by dragging them (e.g., in this example, the pathology tissue diagnosis column 90B) to a recycle bin, represented by recycle bin graphic 106. If desired, the columns can be added again later. In effect, the interactive flow diagram 88 provides the user the ability to dynamically remove endpoints (e.g., columns) from the interactive flow diagram 88, which dynamically updates the data model and the interactive flow diagram 88.

The components involved in this interaction are similar to those used for the repositioning of columns (drag-drop), but here the drop-position is a remove-position (i.e., the recycle bin).

Figure 12A:
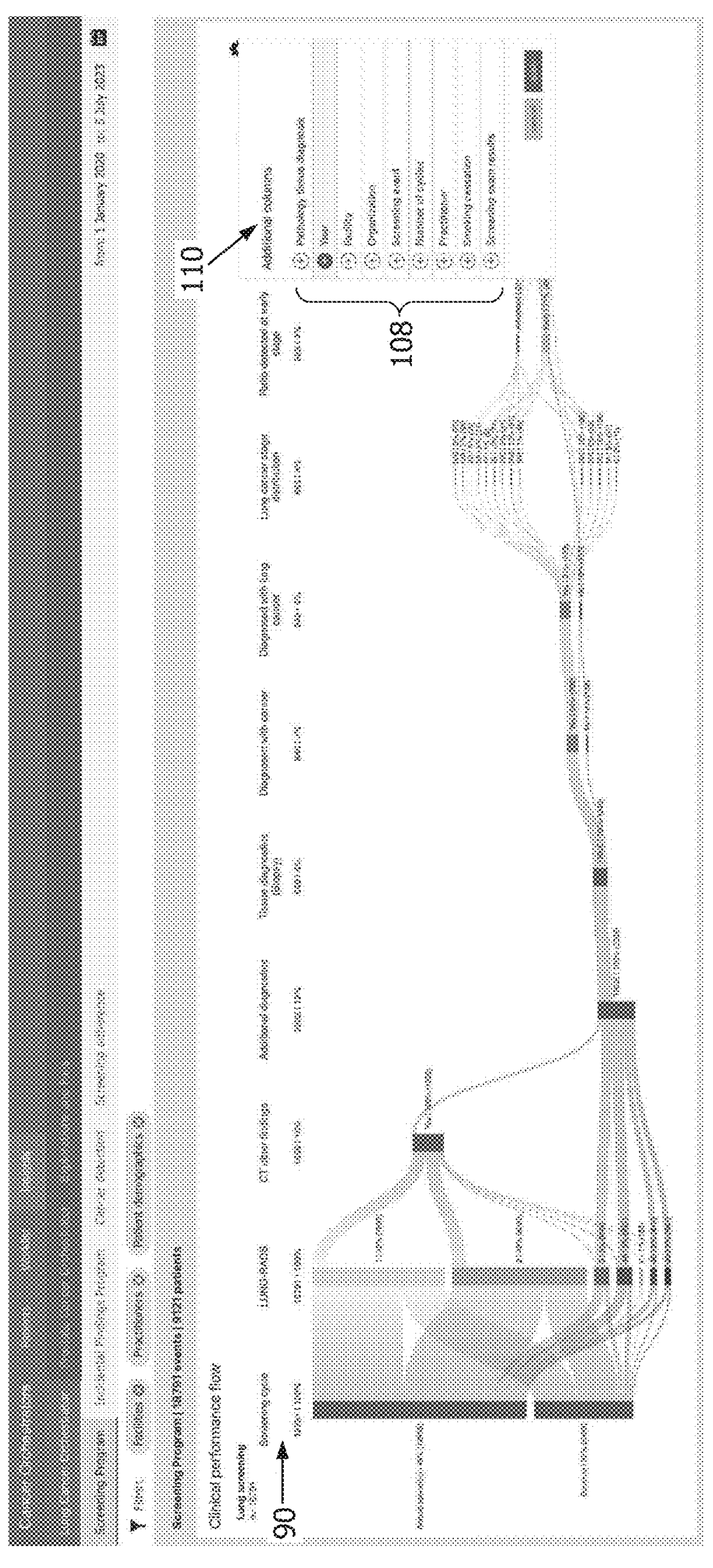
FIGS. 12A-12B are screen diagrams that illustrate an embodiment of the example interactive flow diagram enabling the addition and/or re-ordering of columns, in accordance with an embodiment of the invention.
Figure 12B:
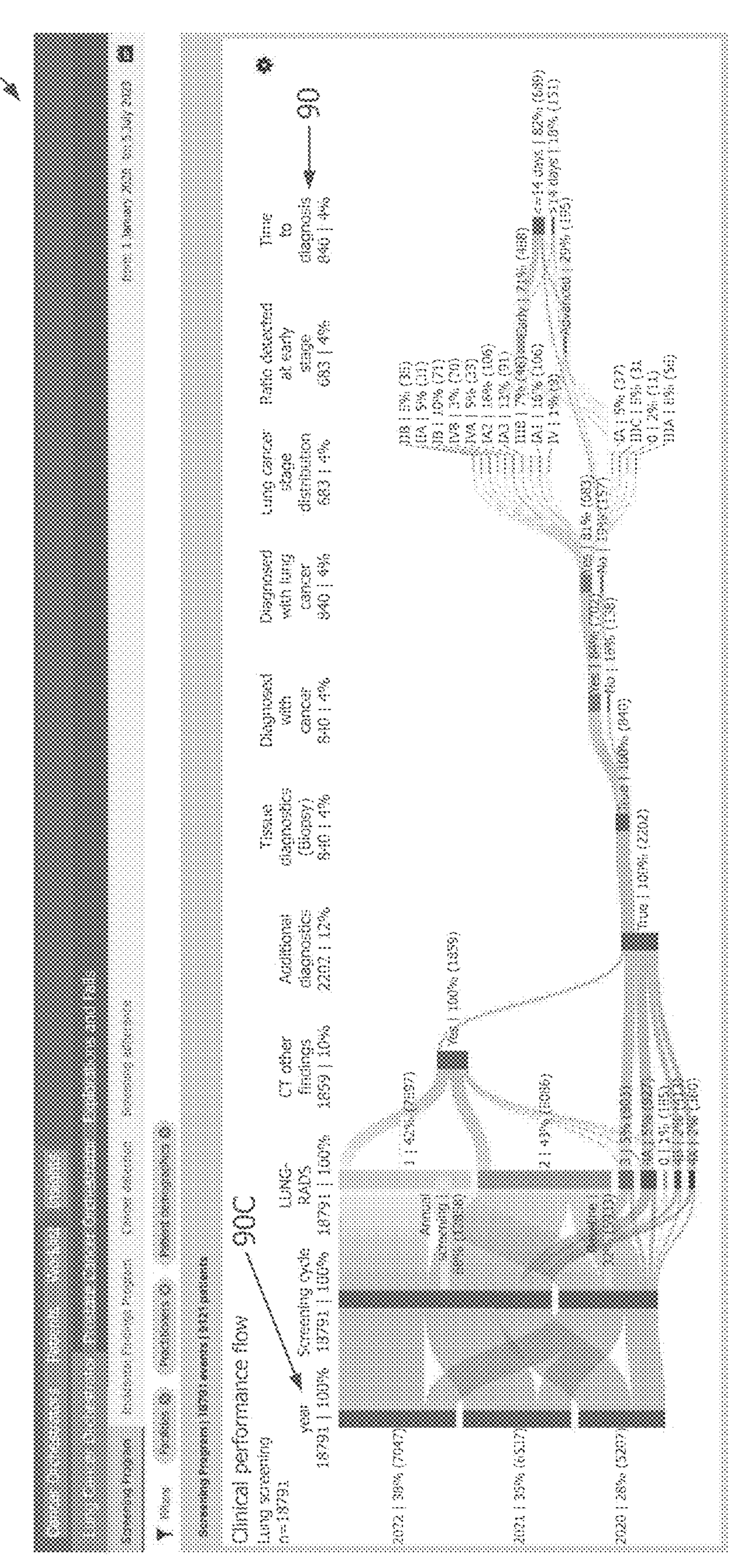

FIGS. 12A-12B illustrate an embodiment of the example interactive flow diagram 88 enabling the addition and/or re-ordering of columns 90. Referring to FIG. 12A, the interactive flow diagram 88 is shown along with an additional columns panel 108 accessed via user selection of the menu item named additional columns 110. The additional columns panel 108 includes a plurality of column options, including pathology tissue diagnosis, year, facility, organization, screening event, and number of cycles, to name a few examples. Through user selection of options from the additional columns panel 108, the user is provided with the ability to add columns 90 to the interactive flow diagram 88. In this example, a column 90 corresponding to a year in which the patients were screened is selected (which may be visually represented, in this example, by a change in color or highlight), with the resulting interactive flow diagram 88 shown in FIG. 12B. In FIG. 12B, the year of the screening exam is positioned as the first column, column 90C of the flow diagram 88. The involved component internal source components are similar as in the previously described interaction examples of repositioning/removing columns, and hence discussion of the same is omitted here for brevity.

Figure 12C:
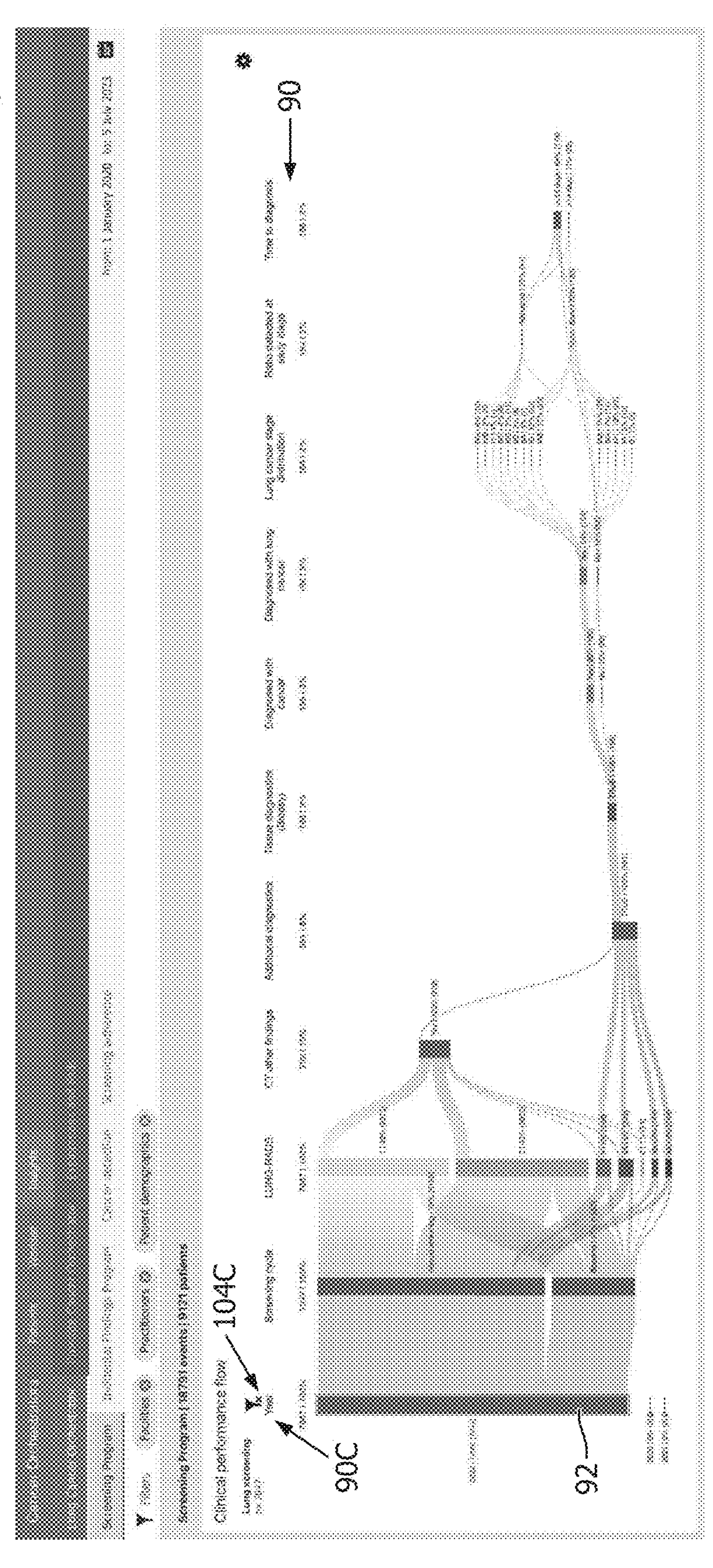
FIG. 12C is a screen diagram that illustrates an embodiment of an example interactive flow diagram enabling filtering using an added column, in accordance with an embodiment of the invention.

FIG. 12C is the interactive flow diagram 88 of FIG. 12B, with an illustration of how filtering is enabled via one of the nodes 92 (e.g., the year 2020 in this example) in the added column 90C, as reflected by the filtering icon 104C located above the column 90C. In some embodiments, the interactive flow diagram 88 enables the user to perform one or a combination of interactions with the interactive flow diagram 88, including adding column(s) and/or filtering on one or more of the nodes in the added column(s).

Figure 13:
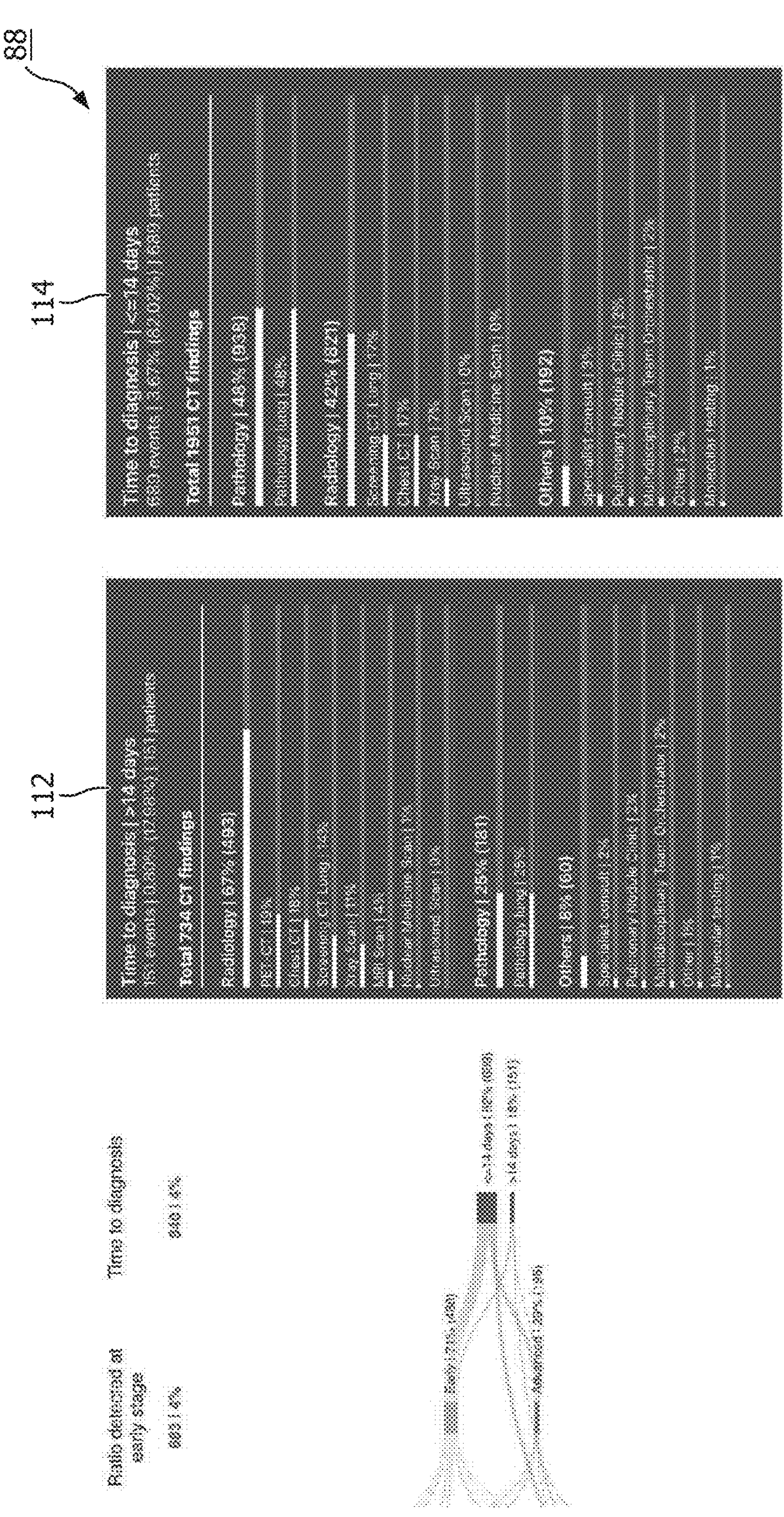
FIG. 13 is a screen diagram that illustrates an embodiment of the example interactive flow diagram enabling a user to select plural populations and extract differences between them, in accordance with an embodiment of the invention.

In some embodiments, the user is provided the ability to flexibly select two or more sub-populations from the interactive flow diagram 88 and extract important differences in flow towards the endpoint of interest. For instance, and referring to FIG. 13, shown is a portion of the interactive flow diagram 88 selected by the user that includes ratio detected at early stage and time to diagnosis. The interactive flow diagram 88 responsively displays two sub-panels, including time to diagnosis >14 days panel 112 and time to diagnosis <=14 days panel 114. The panels 112 and 114 highlight differences in diagnostic follow-up between these two sub-populations. For instance, inspection of the panels 112, 114 reveals that the sub-population with time to diagnosis >14 days has received more PET-CT and MRI scans than the time to diagnosis <=14 days. In general, the interactive flow diagram 88 enables the user to select the population in which the time to diagnosis was above a defined threshold and compares it to the group below the defined threshold.

Note that time to diagnosis is one illustrative example, and the interactive flow diagram 88 enables important differences in flow characteristics to be highlighted for other categories, including between patients diagnosed with advanced stage versus with early stage cancer. For instance, the user may be provided the ability to evaluate if early stage lung cancers were more frequently found via annual screening than via the baseline screening. The interactive flow diagram 88 may be used to highlight differences between facilities, institutes, regions from which patients were recruited, among other comparisons. In some embodiments, the interactive flow diagram 88 enables the user to configure control groups with respect to a benchmark. For example, the user may configure the benchmark for a percentage of patients detected at early stages and display their hospital's numbers versus the benchmark.

Another example in which the interactive flow diagram 88 provides the user the ability to flexibly select two or more sub-populations from the interactive flow diagram 88 and extract important differences in flow towards the endpoint of interest is illustrated in FIG. 14, which shows a patient list screen 116 invoked through interaction with the interactive flow diagram 88. As similarly explained above, certain user interactions with the flow diagram 88 may be accomplished using programmed combination functionality associated with the input device (e.g., left click, right click, mouse plus keyboard, verbal commands, etc.) and/or interactions that invoke menus or pop-up windows, to name a few examples. In one embodiment, the user is provided the ability to transition between a full program overview (e.g., as provided by the entire interactive flow diagram 88) to a sub-cohort (e.g., a node or combination of nodes) and to the individual patient level via the patient list screen 116. The patient list screen 116 may be extracted via a list of unique patient identifiers for the selected node, as well as events of these patients. The patient list screen 116 comprises a list of individual patients in the selected cohorts (e.g., by patient medical record numbers and other patient details). This information may subsequently be used to display additional information and charts for these patients. In some embodiments, the user has the ability to select one of the patients and make comparisons to similar patients.

Figure 15:
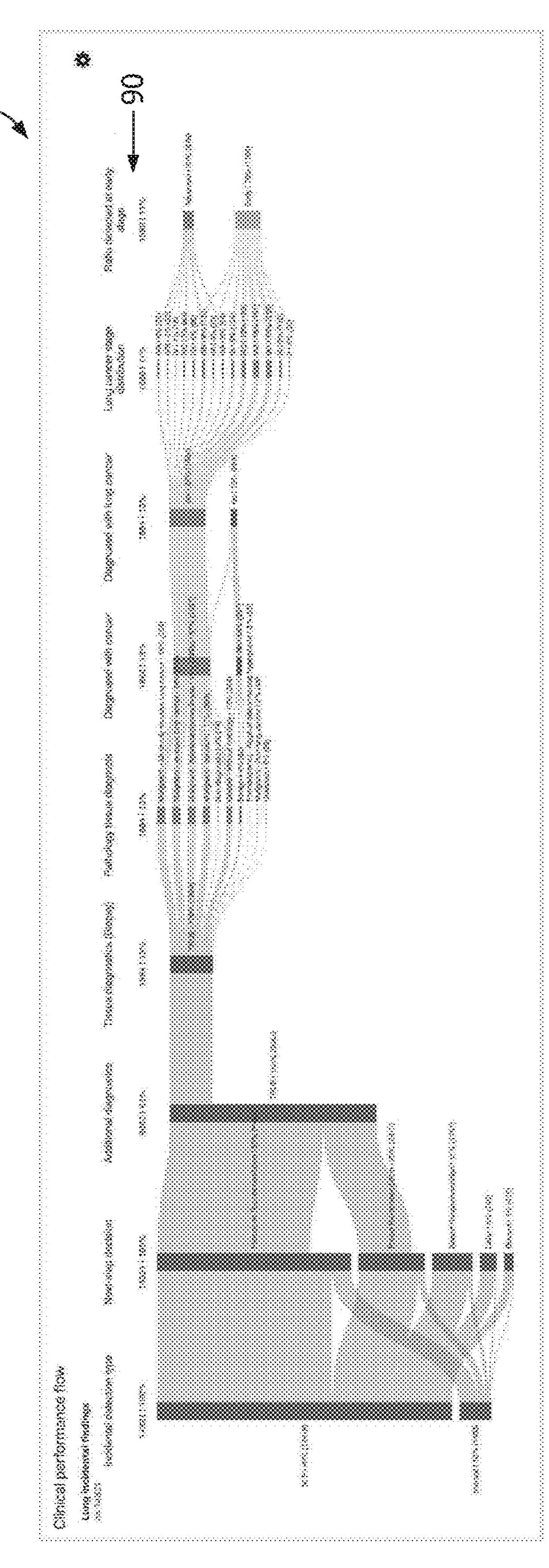
FIG. 15 is a screen diagram that illustrates an embodiment of the example interactive flow diagram presenting incidental findings associated with functionality of a lung cancer orchestrator, in accordance with an embodiment of the invention.

Though the example illustrations above for the interactive flow diagram 88 are shown and described in the context of a screening program (e.g., via selection of the screening program tab) for the orchestrator application, the interactive flow diagram 88 may be used in similar manner for other functionality of the orchestrator. In other words, other interactive flow diagrams may be generated with differently configured columns. For instance, and referring to FIG. 15, shown is an interactive flow diagram 88A for the incidental findings program (e.g., via selection of the incidental findings program tab of the orchestrator). In the depicted example, the interactive flow diagram 88A comprises columns 90 corresponding to lung incidental findings, with nodes corresponding to NLP|90% (12918) and manual|10% (1403). The columns 90 include two new column categories in incidental detection type and next-step decision, as well as those similarly used in the aforementioned interactive flow diagram 88 including additional diagnostics, tissue diagnostics (biopsy), pathology tissue diagnosis, diagnosed with cancer, diagnosed with lung cancer, lung cancer stage distribution, and ratio detected at early stage. Similarly, an interactive flow diagram may be generated and displayed for the cancer detection functionality (cancer tab selection). In some embodiments, the interactive flow diagrams may be displayed on separate pages or may be combined into one overarching flow diagram.

The interactive flow diagrams described herein enable the user to apply various tools and/or infer insights in the analytics and/or diagnoses. In some embodiments, the user has the ability to apply statistical tests for comparisons between sub-populations in the interactive flow diagram, such as to evaluate significance of differences. In some embodiments, the user has the ability to infer probabilities of a patient (or sub-group) with certain characteristics of flows into the one or other category (e.g., node), which also enables a user to anticipate how these probabilities may change, upon adding an additional characteristic and to analyze the downstream effect on all flows. For example, the effect of the introduction of a biomarker test with a known predictive value on the diagnostic outcome (e.g. based on literature) on the downstream flows may be simulated, which can enable cost-effectiveness analyses with/without the use of the biomarker and aid in improving the early detection program's efficacy.

In some embodiments, the interactive flow diagram may be applied to the genomics fields to link diseases/cancers/genetic variants/sub-types of variants/chromosomes. For instance, the interactive flow diagram may be used to visualize what sub-set of patients among all patients with a specific genetic variant of appear to have cancer and of all patients with a second (additional) genetic variant, by how much did that increase the likelihood of getting cancer.

In some embodiments, the interactive flow diagram may be used to visualize treatment pathways and outcomes of treatments.

In some embodiments, the interactive flow diagram has a self-service component (e.g., the user may configure the flows and columns of interest and save the configuration files).

Note that the patient management application (e.g., orchestrator) and/or analytics and the interactive flow diagram generation system 18 (FIG. 2A) and associated functionality (e.g., the interactive flow diagram) may be implemented as part of a cloud computing environment (or other server network) that serves one or more clinical and/or research facilities. When implemented as part of a cloud service or services, one or more computing devices may comprise an internal cloud, an external cloud, a private cloud, or a public cloud (e.g., commercial cloud). For instance, a private cloud may be implemented using a variety of cloud systems including, for example, *Eucalyptus* Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture of the computing devices may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, computing devices used in the implementation of the disclosed embodiments may be configured into multiple, logically-grouped servers (run on server devices), referred to as a server farm. The computing devices may be geographically dispersed, administered as a single entity, or distributed among a plurality of server farms. The computing devices within each farm may be heterogeneous. One or more of the computing devices may operate according to one type of operating system platform (e.g., WINDOWS NT, manufactured by Microsoft Corp. of Redmond, Wash.), while one or more of the computing devices may operate according to another type of operating system platform (e.g., Unix or Linux). The computing devices may be logically grouped as a farm that may be interconnected using a wide-area network (WAN) connection or medium-area network (MAN) connection. The computing devices may each be referred to as, and operate according to, a file server device, application server device, web server device, proxy server device, or gateway server device.

Note that cooperation between devices (e.g., clinician computing devices) of other networks and the devices of the cloud (and/or cooperation among devices of the cloud) may be facilitated (or enabled) through the use of one or more application programming interfaces (APIs) that may define one or more parameters that are passed between a calling application and other software code such as an operating system, library routine, and/or function that provides a service, that provides data, or that performs an operation or a computation. The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

As should be appreciated by one having ordinary skill in the art, one or more computing devices of the cloud platform (or other platform types), as well as of other networks communicating with the cloud platform, may be embodied as an application server, computer, among other computing devices. In that respect, one or more of the computing devices comprises one or more processors, input/output (I/O) interface(s), one or more user interfaces (UI), which may include one or more of a keyboard, mouse, microphone, speaker, tactile device (e.g., comprising a vibratory motor), touch screen displays, etc., and memory, all coupled to one or more data busses.

The memory may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory may store a native operating system, one or more native applications, emulation systems, or emulated applications for any of a variety of operating systems and/or emulated hardware platforms, emulated operating systems, etc. In some embodiments, a separate storage device may be coupled to the data bus or as a network-connected device.

The storage device may be embodied as persistent memory (e.g., optical, magnetic, and/or semiconductor memory and associated drives). The memory comprises an operating system (OS) and application software, including the interactive flow diagram generation system 18 and the patient management application and/or analytics application described herein.

Execution of the software may be implemented by one or more processors under the management and/or control of the operating system. The processor may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing device.

When certain embodiments of the computing device are implemented at least in part with software (including firmware), embodiments of the invention provide for a computer program product comprising a set of computing device executable instructions for performing the method of any of the previously described embodiments of the method. It should be further noted that the software may be stored on a variety of non-transitory computer-readable (storage) medium for use by, or in connection with, a variety of computer-related systems or methods. In the context of this document, a computer-readable storage medium may comprise an electronic, magnetic, optical, or other physical device or apparatus that may contain or store a computer program (e.g., executable code or instructions) for use by or in connection with a computer-related system or method. The software may be embedded in a variety of computer-readable storage mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. For instance, in addition to the example applications/platforms described herein (e.g., IntelliSpace Precision Medicine (ISPM), Lung analytics, embedded in the ISPM Lung Cancer Orchestrator application, including screening and incidental findings applications), certain embodiments of the interactive flow diagram generation system 18 may be deployed in or in association with pathway analytics (e.g., embedded in an ISPM Oncology Pathways application), other products or projects involving analytics (e.g., PerformanceBridge), future analytics applications (e.g., genome analytics, prostate analytics), orchestrators (e.g. care orchestrator, oncology orchestrator, lung cancer orchestrator, prostate cancer orchestrator, cardiology care orchestrator, neurology orchestrator, sleep orchestrator), or other workflow solutions (e.g. cardiology applications, radiology informatics applications) and their associated incidental findings management applications or other findings management and scheduling and reporting applications.

Figure 16:
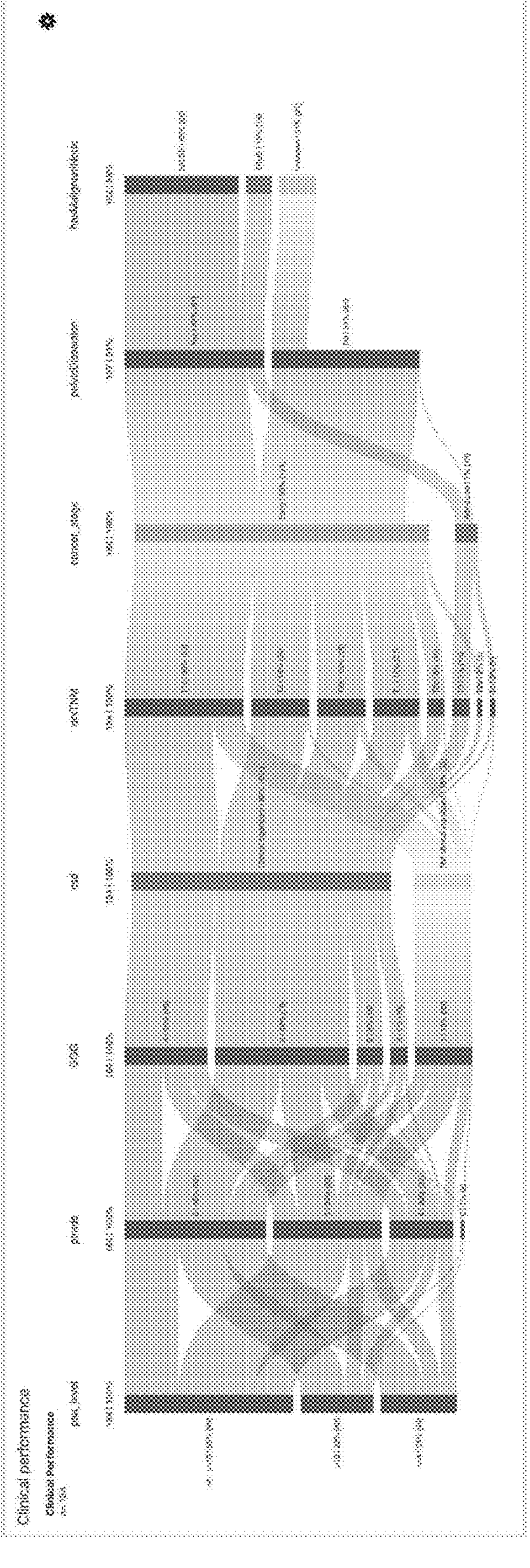
FIG. 16 is a screen diagram that illustrates an example patient flow visualization of oncology pathways using the example of prostate cancer, in accordance with an embodiment of the invention.

In one embodiment, the interactive flow diagram may be used to visualize treatment pathways and outcomes of treatments. For instance, and referring to FIG. 16, shown is an example patient flow visualization of a prostate cancer pathway, in which besides diagnostic information, treatment information is also added. Specifically, FIG. 16 shows an example patient flow visualization of oncology pathways, with an example of prostate cancer. Besides diagnostic information, the patient flow visualization also displays treatment information. Abbreviations in the figure are as follows: PSA: prostate specific antigen, PIRADS: Prostate Imaging Reporting and Data System, GGG: Gleason Grade Group, CSD: Clinically Significant Disease, drxTNM and Cancer_Stage: Prostate Cancer Staging, HormoneTherapy and pelvicDissection: prostate cancer treatments. Note that this example is merely illustrative of extending the interactive flow diagram embodiments described herein to other applications for visualization, and it should be appreciated that other treatment pathways may be visualized in some embodiments and hence are contemplated to be within the scope of the invention. A variety of treatments may be addressed in the visualization including for example immunotherapy, gene therapy, ablation therapy, surgical resection, palliative therapy, use of device (e.g., continuous positive airway pressure (CPAP) machine), medicine, wait-and-see approaches in delaying treatment, or a combination thereof. The timing of the treatments may be concurrent or serial or a combination thereof. The treatments may be fractional such that the treatment is delivered in separate doses at different times. The ablation therapy may comprise any of thermal therapy (using laser, ultrasound, radiofrequency or microwave energy sources); photodynamic therapy (using a combination of a photosensitizing drug and an activating light source); radiation treatment using either implanted radioactive sources or external ionizing radiation beams; mechanical or other surgical devices to perform a partial prostatectomy; local injection of an anti-cancer agent (drug, biologic, gene, noxious agent); or a combination thereof. The visualization may further address lifestyle behaviour changes related to, for example, diet or nutrition, sleep, stress, social interaction, exercise, etc.

In general, certain embodiments of the interactive flow diagram generation system 18 may be applicable to various medical domains, including oncology, cardiology, etc., any program or domain with a need to track flow, throughput, or resource usage, any domain where spreadsheets are to keep track of patients, outcomes and resources, and/or any situation in which there is a flow or sequence of events, event results, decisions, and in which a user is interested in analytical insights on these events/results/decisions.

Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. Further, each method claim may be performed by a computing device, system, or by a non-transitory computer readable medium. The computing device may include memory in the form of a non-transitory computer readable medium, or may include one or more each of a memory and a non-transitory computer readable medium. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms.

A portion of the disclosure of this patent document contains material, including without limitation, software instructions and/or program code that is subject to copyright protection. The copyright owner has no objection to the facsimile reproduction by anyone of the patent document or the patent disclosure, as it appears in the Patent and Trademark Office patent file or records but otherwise reserves all copyright rights whatsoever.

At least the following is claimed:

1. A method for presenting information along plural stages of patient care, the method comprising:
- initializing an interactive flow diagram based on data, the interactive flow diagram based on an underlying data model, the interactive flow diagram comprising nodes comprising an aggregated visual representation of key-value pairs, columns comprising a stacked bar visualization of the nodes, and links between the nodes, wherein each link connects a first node and a second node, and wherein each link has a visual height that represents a size of components contained in both the first node and second node connected by the link;
- displaying the interactive flow diagram; and
- dynamically updating the interactive flow diagram based on user interactions with the interactive flow diagram, the interactions resulting in updates to the underlying data model that change an arrangement of at least one of the nodes, the columns, or the links.

2. The method of claim 1, further comprising receiving the data from one or a combination of a spreadsheet data or an analytics database.

3. The method of claim 1, further comprising providing aggregated information based on user input over one of the nodes, the aggregated information providing further detail about the one of the nodes.

4. The method of claim 1, further comprising isolating a sub-population of one of the nodes based on user input at the one of the nodes.

5. The method of claim 1, further comprising providing demographics in graphs adjacent the interactive flow diagram based on user selection of one of the nodes.

6. The method of claim 1, further comprising repositioning or removing one of the columns based on user input corresponding to drag-and-drop functionality.

7. The method of claim 1, further comprising filtering one or more nodes or one or more graphs based on user selection of the one or more nodes.

8. The method of claim 1, further comprising highlighting differences between two or more sub-populations based on user selection of the two or more sub-populations for a given one of the columns.

9. The method of claim 1, further comprising providing information for an individual patient for a selected cohort.

10. The method of claim 1, wherein the interactive flow diagram further comprises treatment pathways and/or outcomes of treatments.

11. The method of claim 1, wherein the displaying comprises displaying the interactive flow diagram in a single view.

12. The method of claim 1, wherein the displaying comprises displaying the interactive flow diagram as a standalone analytics tool, or one or a combination of in conjunction with an existing analytics application as a custom chart or in conjunction with a patient management application.

13. The method of claim 1, wherein patient management application comprises a lung cancer orchestrator.

14. The method of claim 1, wherein the first node is a source node and the second node is a target node, and wherein size of components contained in both the first node and second node connected by the link is measured by a difference between the source node and the target node.

15. A computing device, comprising a memory comprising instructions, a user interface, and one or more processors, wherein the one or more processors is configured to implement the instructions to perform a method comprising:
- initializing an interactive flow diagram based on data, the interactive flow diagram based on an underlying data model, the interactive flow diagram comprising nodes comprising an aggregated visual representation of key-value pairs, columns comprising a stacked bar visualization of the nodes, and links between the nodes, wherein each link connects a first node and a second node, and wherein each link has a visual height that represents a size of components contained in both the first node and second node connected by the link;
- displaying, via the user interface, the interactive flow diagram; and
- dynamically updating the interactive flow diagram based on user interactions with the interactive flow diagram, the interactions resulting in updates to the underlying data model that change an arrangement of at least one of the nodes, the columns, or the links.

16. The computing device of claim 15, wherein the first node is a source node and the second node is a target node, and wherein size of components contained in both the first node and second node connected by the link is measured by a difference between the source node and the target node.

17. The computing device of claim 15, wherein the method further comprises highlighting differences between two or more sub-populations based on user selection of the two or more sub-populations for a given one of the columns.

18. A non-transitory computer readable storage medium comprising instructions that, when executed by one or more hardware processors, cause the one or more hardware processors to perform a method comprising:
- initializing an interactive flow diagram based on data, the interactive flow diagram based on an underlying data model, the interactive flow diagram comprising nodes comprising an aggregated visual representation of key-value pairs, columns comprising a stacked bar visualization of the nodes, and links between the nodes, wherein each link connects a first node and a second node, and wherein each link has a visual height that represents a size of components contained in both the first node and second node connected by the link;
- displaying the interactive flow diagram; and
- dynamically updating the interactive flow diagram based on user interactions with the interactive flow diagram, the interactions resulting in updates to the underlying data model that change an arrangement of at least one of the nodes, the columns, or the links.

19. The non-transitory computer readable storage medium of claim 18, wherein the first node is a source node and the second node is a target node, and wherein size of components contained in both the first node and second node connected by the link is measured by a difference between the source node and the target node.

20. The non-transitory computer readable storage medium of claim 18, wherein the method further comprises highlighting differences between two or more sub-populations based on user selection of the two or more sub-populations for a given one of the columns.

* * * * *